(12) United States Patent
Brash et al.

(10) Patent No.: US 6,569,644 B2
(45) Date of Patent: May 27, 2003

(54) ISOLATED AND PURIFIED 12R-LIPOXYGENASE PROTEIN AND NUCLEIC ACIDS

(75) Inventors: Alan R. Brash, Nashville, TN (US); William E. Boeglin, Nashville, TN (US); Richard B. Kim, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/853,053

(22) Filed: May 11, 2001

(65) Prior Publication Data

US 2002/0037554 A1 Mar. 28, 2002

Related U.S. Application Data

(62) Division of application No. 09/510,621, filed on Feb. 22, 2000, now abandoned, which is a division of application No. 09/087,727, filed on May 29, 1998, now Pat. No. 6,103,496.

(51) Int. Cl.[7] .............................. C12P 21/06; C12N 9/00; C07K 1/00; C07K 14/00
(52) U.S. Cl. ...................... 435/69.1; 435/183; 435/325; 530/350; 530/387.1; 424/130.1
(58) Field of Search .............................. 530/350, 387.1; 435/69.1, 69.2, 183, 6, 325; 424/130.1; 514/2–21; 536/23.1, 23.5

(56) References Cited

U.S. PATENT DOCUMENTS

| 5,102,670 | A | 4/1992 | Abraham et al. |
|---|---|---|---|
| 5,182,367 | A | 1/1993 | Gillard et al. |
| 5,234,933 | A | 8/1993 | Marnett et al. |
| 5,326,902 | A | 7/1994 | Seipp et al. |
| 5,530,114 | A | 6/1996 | Bennett et al. |
| 5,696,076 | A | 12/1997 | Gentz et al. |

FOREIGN PATENT DOCUMENTS

| EP | 0325773 | 8/1989 |
|---|---|---|
| EP | 0384750 | 8/1990 |
| WO | WO 93/25521 | 12/1993 |
| WO | WO 94/05777 | 3/1994 |
| WO | WO 95/18609 | 7/1995 |
| WO | WO 95/25178 | 9/1995 |
| WO | WO 96/34943 | 11/1996 |

OTHER PUBLICATIONS

Krieg et al., Biochim. Biophys. Acta., vol. 1391, p. 7–12, (1998).

Sun et al., "Human 12(R)–Lipoxygenase and the Mouse Ortholog," Journal of Biological Chemistry, vol. 273, p. 33540–33547, (1998).

*Primary Examiner*—Sean McGarry
*Assistant Examiner*—Janet L. Epps
(74) *Attorney, Agent, or Firm*—Jenkins & Wilson, P.A.

(57) ABSTRACT

Isolated and purified lipoxygenase proteins and nucleic acids are described. Particularly, a novel human 12R-lipoxygenase (12R-LO) protein and cDNA are described. Recombinant host cells, recombinant nucleic acids and recombinant proteins are also described, along with methods of producing each. Isolated and purified antibodies to 12R-LO, and methods of producing the same, are also described.

18 Claims, 9 Drawing Sheets

FIG. 2A

```
ATGGCCACCTACAAAGTCAGGGTGGCCACAGGCACCGACCTCTTGTGTGGAACACGGGAC    60
 M   A   T   Y   K   V   R   V   A   T   G   T   D   L   L   S   G   T   R   D    20
TCCATCTCACTGACCATTGTGGGGACACAAGGAGAGCCATAAGCAGCTGCTGAACCAC     120
 S   I   S   L   T   I   V   G   T   Q   G   E   S   H   K   Q   L   L   N   H    40
TTTGGGAGAGACTTTGCAACTGGGGCGGTGGGCCAGTACACCGTGCAGTGCCCTCAGGAC   180
 F   G   R   D   F   A   T   G   A   V   G   Q   Y   T   V   Q   C   P   Q   D    60
CTGGGGTGAGCTCATCATCATCCGCCTGCACAAAGAGCGGTACGCCTTCTTCCCCAAGGAC  240
 L   G   E   L   I   I   I   R   L   H   K   E   R   Y   A   F   F   P   K   D    80
CCTTGGTACTGCAACTATGTGCAGATCTGTGCCCCCAACGGCCGTATCTACCACTTCCCC   300
 P   W   Y   C   N   Y   V   Q   I   C   A   P   N   G   R   I   Y   H   F   P    100
GCCTACCAGTGGATGGATGGCTACGAGACCCTGGCACTCCGGGAGGCCACAGGAAAGACA   360
 A   Y   Q   W   M   D   G   Y   E   T   L   A   L   R   E   A   T   G   K   T    120
ACAGCAGATGACTCGCTCCCCGTCCTCCTGGAGCACAGAAAGAGGAGATCAGAGCCAAG    420
 T   A   D   D   S   L   P   V   L   L   E   H   R   K   E   E   I   R   A   K    140
CAGGACTTCTACCACTGGCGAGTCTTTCTTCCTGGCCTGCCCAGCTATGTGCACATTCCC   480
 Q   D   F   Y   H   W   R   V   F   L   P   G   L   P   S   Y   V   H   I   P    160
```

FIG. 2B

```
AGTTACCGCCCCTCCGGTGCGGAGGCATCGCAACCCCAACCGGCCTGAGTGGAATGGCTAT  540
 S  Y  R  P  P  V  R  R  H  R  N  P  N  R  P  E  W  N  G  Y
ATTCCGGGATTCCCAATTCTCATCAACTTTAAGGCCACCAAGTTCCTGAACTTAAATCTC   600
 I  P  G  F  P  I  L  I  N  F  K  A  T  K  F  L  N  L  N  L
CGCTACTCCTTCCTCAAGACGGCCCTCCTCTTCGTTCGCCTGGGGCCCATGGCACTGGCT   660
 R  Y  S  F  L  K  T  A  S  F  F  V  R  L  G  P  M  A  L  A
TTCAAAGTCCGCGGCCTGTTGGACTGCAAACATTCGTGGAAGAGGCTGAAGGACATTAGG   720
 F  K  V  R  G  L  L  D  C  K  H  S  W  K  R  L  K  D  I  R
AAAATTTCCCTGGCAAGAAATCTGTCGTCTCCGAGTACGTGGCCGAGCACTGGGCAGAG    780
 K  I  F  P  G  K  K  S  V  V  S  E  Y  V  A  E  H  W  A  E
GACACCTTCTTTGGGTACCAGTACCTCAACGGCGTCAACCCCGGCCTGATCCGCCGCTGC   840
 D  T  F  F  G  Y  Q  Y  L  N  G  V  N  P  G  L  I  R  R  C
ACGGCGGATCCCAGACAAGTTCCCCGTCACAGACGACATGGTGGCTCCGTTCCTGGGCGAG  900
 T  R  I  P  D  K  F  P  V  T  D  D  M  V  A  P  F  L  G  E
GGAACGTGCTTGCAAGCGGAGCTGGAGAAGGGAACATTTACCTGGCCGACTACCGCCATC   960
 G  T  C  L  Q  A  E  L  E  K  G  N  I  Y  L  A  D  Y  R  I
```
 180
 200
 220
 240
 260
 280
 300
 320

FIG. 2C

```
ATGGAGGGCATCCCCACCGTGGAGCTCAGCGGAGCCGGAAGCAGCACCACTGCGCCCCCTC  1020
 M  E  G  I  P  T  V  E  L  S  G  R  K  Q  H  H  C  A  P  L    340
TGCCTGCTGCACTTTGGACCCGAGGGCAAGATGATGCCCATCGCCCATCCAGCTCAGCCAG  1080
 C  L  H  F  G  P  E  G  K  M  M  P  I  A  I  Q  L  S  Q       360
ACCCCTGGGCCAGATTGCCCCATCTTCCTGCCCAGTGATTCTGAGTGGGACTGGCTGCTA   1140
 T  P  G  P  D  C  P  I  F  L  P  S  D  S  E  W  D  W  L  L    380
GCCAAGACGTGGGTACGCTATGCGGAGTTCTACAGCCACGAGGCCATCGCCACCTGCTG    1200
 A  K  T  W  V  R  Y  A  E  F  Y  S  H  E  A  I  A [H] L  L    400
GAGACACACCTCATTGCTGAGGCCTTCTGCCTTGCTCTGAGGAACCTGCCCATGTGC      1260
 E  T [H] L  I  A  E  A  F  C  L  A  L  L  R  N  L  P  M  C    420
CACCCCCCTCTACAAGCTCCTCATCCCCATACCCGATACACCGTCCAGATCAACAGCATT   1320
 H  P  L  Y  K  L  L  I  P  H  T  R  Y  T  V  Q  I  N  S  I    440
GGCCGGGCCGTTCTCCTCAATGAGGGGGGCCTCTCTGCCAAGGGCATGTCCCTGGGCGTG   1380
 G  R  A  V  L  L  N  E  G  G  L  S  A  K  G  M  S  L  G  V    460
GAAGGCTTTGCTGGGGTGATGGTACGGGCTCTCTGTCGGAGCTCACCTATGACAGCCTCTAC 1440
 E  G  F  A  G  V  M  V  R  A  L  S  E  L  T  Y  D  S  L  Y    480
```

FIG. 2D

```
CTCCCCAATGACTTTGTGGAGCGTGGGGTCCAGGACCTGCCTGGATATTACTACCGCGAT  1500
 L  P  N  D  F  V  E  R  G  V  Q  D  L  P  G  Y  Y  Y  R  D   500
GACAGCTTGGCGGTGTGGAATGCACTGGAGAAGTATGTGACGGAGATCATCACCTATTAT  1560
 D  S  L  A  V  W  N  A  L  E  K  Y  V  T  E  I  I  T  Y  Y   520
TACCCGAGTGACGCAGCCGTGGAGGGTGATCCGGAATTGCAGTCTTGGGTGCAGGAAATA  1620
 Y  P  S  D  A  A  V  E  G  D  P  E  L  Q  S  W  V  Q  E  I   540
TTTAAAGAGTGCCTCCTGGGGCGGGAGAGCTCAGGCTTCCCTAGGTGCTTGCGAACCGTG  1680
 F  K  E  C  L  L  G  R  E  S  S  G  F  P  R  C  L  R  T  V   560
CCTGAGCTGATCCGATATGTCACTATAGTCATCTACACCTGCTCTGCCAAGCACGCTGCT  1740
 P  E  L  I  R  Y  V  T  I  V  I  Y  T  C  S  A  K [H] A  A   580
GTCAACACAGGCCAGATGGAGTTCACCGCCTGGATGCCCAACTTCCCAGCTTCCATGCGG  1800
 V [N] T  G  Q  M  E  F  T  A  W  M  P  N  F  P  A  S  M  R   600
AATCCACCGATTCAGACTAAGGGGCTGACCACTCTGGAGACCTTCATGGACACGTTGCCG  1860
 N  P  P  I  Q  T  K  G  L  T  T  L  E  T  F  M  D  T  L  P   620
GATGTGAAGACCACGTGCATCACGCTGCTCTGGACCCTCAGCCGAGAGCCTGAC         1920
 D  V  K  T  T  C  I  T  L  L  V  L  W  T  L  S  R  E  P  D   640
```

FIG. 2E

```
GACAGGGGCGGCCCTGGGACACTTCCCGGACATTCACTTCGTGGAGGAGGCCCCGCGGAGG   1980
 D   R   R   P   L   G   H   F   P   D   I   H   F   V   E   E   A   P   R   R    660
AGCATAGAGAGGCGTTCCGCCAGCGCCTGAACCAGATCTCACACGACATCCGCCAGCGCAAC   2040
 S   I   E   A   F   R   Q   R   L   N   Q   I   S   H   D   I   R   Q   R   N    680
AAGTGCCTTCCCATCCCCTACTACTACCTGGACCCGGTGCTGATTGAGAACAGCATTTCT    2100
 K   C   L   P   I   P   Y   Y   Y   L   D   P   V   L   I   E   N   S   I   S     700
ATT                                                              2103
 I                                                                701
```

SCHEME: Pro-R 10-$^3$H abstraction by 12R-Lipoxygenase

ISOLATED AND PURIFIED 12R-LIPOXYGENASE PROTEIN AND NUCLEIC ACIDS

This application is a divisional of U.S. patent application Ser. No. 09/510,621 filed Feb. 22, 2000, now abandoned, which is a divisional of U.S. patent application Ser. No. 09/087,727 filed May 29, 1998, now U.S. Pat. No. 6,103,496, the entire content of each herein incorporated by reference.

GRANT STATEMENT

This work was supported by NIH grant GM-53638. Human keratinocytes were provided by the Tissue Core Laboratory of the Vanderbilt Skin Disease Research Center, which is supported by grant 5P30 AR41943-03 from the NIH/NIAMS. The U.S. Government has certain rights in the invention.

TECHNICAL FIELD

The present invention relates generally to isolated and purified lipoxygenase proteins and nucleic acids. More particularly, the present invention relates to an isolated and purified 12R-lipoxygenase and an isolated and purified polynucleic acid encoding the same.

The publications and other materials used herein to illuminate the background of the invention, and in particular cases, to provide additional details respecting the practice, are incorporated herein by reference, and for convenience, are referenced by author and date in the following text, and respectively group in the appended list of references.

| Table of Abbreviations | |
|---|---|
| 12R-LO | 12R-lipoxygenase |
| 12R-HETE | 12R-hydroxyeicosatetraenoic acid |
| BSA | Bovine serum albumin |
| GC-MS | Gas chromatography-Mass spectroscopy |
| HAT | Cell culture media comprising hypoxanthine, aminopterin, and thymidine |
| HETE | Hydroxyeicosatetraenoic acid |
| HPETE | Hydroperoxyeicosatetraenoic acid |
| H(P)ETE | Either Hydroxyeicosatetraenoic acid or Hydroperoxyeicosatetraenoic acid |
| HODE | Hydroxyoctadecadienoic acid |
| HPLC | High pressure liquid chromatography |
| KLH | Keyhole limpet hemocyanin |
| PCR | Polymerase chain reaction |
| PFB | Pentafluorobenzyl ester |
| PMA | Phorbol-12-myristate-13-acetate |
| RACE | Rapid amplification of cDNA ends |

BACKGROUND ART

The lipoxygenases are a structurally related family of non-heme iron dioxygenases that function in the production of fatty acid hydroperoxides. Four lipoxygenases have been identified and cloned in humans. Funk, C. D. (1993) *Prog. Nuc. Acid Res. Mol. Biol.* 45:67–98; Matsumoto et al. (1988) *Proc. Natl. Acad. Sci. USA* 85: 26–30; Dixon et al. (1988) *Proc. Natl. Acad. Sci. USA* 85: 416–420; Funk et al. (1990) *Proc. Natl. Acad. Sci. USA* 87: 5638–5642; Izumi et al. (1990) *Proc. Natl. Acad. Sci. USA* 87:7477–7481; Yoshimoto et al. (1990) *Biochem. Biophys. Res. Comm.* 172:1230–1235; Sigal et al. (1988) *Biochem. Biophys. Res. Comm.* 157:457–464; Brash et al. (1997) *Proc. Natl. Acad Sci. USA* 94:6148–6152). They oxygenate arachidonic acid in different positions along the carbon chain and form the corresponding 5S-, 12S- or 15S-hydroperoxides (hydro(pero)xyeicosatetraenoic acids, H(P)ETEs). Three of these enzymes are known mainly from the blood cell types in which they are strongly expressed—the 5S-lipoxygenase of leukocytes, the 12S-lipoxygenase of platelets, and the 15S-lipoxygenase of reticulocytes, eosinophils and macrophages. While these are the most widely recognized cellular sources, selective expression is documented in other tissues. For example, both the 12S- and 15S-lipoxygenases are detected in skin. Nugteren et al. (1987) *Biochim. Biophys. Acta* 921:135–141; Henneicke-von Zepelin et al. (1991) *J. Invest. Dermatol.* 97:291–297; Takahashi et al. (1993) *J. Biol. Chem.* 268:16443–16448; Hussain et al. (1994) *Amer. J. Physiol.* 266:C243–C253. The fourth of the known human lipoxygenases, a second type of 15S-lipoxygenase, was cloned from skin and this enzyme is also expressed in prostate, lung, and cornea. Brash et al. (1997) *Proc. Natl. Acad Sci. USA* 94:6148–6152.

Interest in the biosynthesis of hydroxy derivatives of arachidonic acid in skin stems from the role of essential fatty acids and their derivatives in the structural integrity of normal epidermis (Burr et al. (1929) *J. Biol. Chem.* 82:345–367; Nugteren et al. (1985) *Biochim. Biophys. Acta* 834, 429–436; Nugteren et al. (1987) *Biochim. Biophys. Acta* 921:135–141), and from the potential involvement of arachidonate metabolites in inflammatory and proliferative skin diseases (Hammarström et al. (1975) *Proc. Natl. Acad. Sci. USA* 72:5130–5134; Hussain et al. (1994) *Am. J. Physiol.* 266:C243–C253; Ziboh, V. A. (1996) *Lipids* 31:S249–S253). The major products of arachidonic acid metabolism in normal human skin or keratinocytes are 12-hydroxy- and 15-hydroxyeicosatetraenoic acids (12-HETE and 15-HETE) (Nugteren et al. (1987) *Biochim. Biophys. Acta* 921:135–141; Hammarström et al. (1975) *Proc. Natl. Acad. Sci. USA* 72:5130–5134; Hussain et al. (1994) *Am. J. Physiol.* 266:C243–C253; Ziboh, V. A. (1996) *Lipids* 31:S249–S253; Burrall et al. (1988) *J. Invest. Dermatol.* 4:294–297; Green, F. A. (1989) *J. Invest. Dermatol.* 93:486 –491; Holtzman et al. (1989) *J. Clin. Invest.* 84:1446–1453; Henneicke-von Zepelin et al. (1991) *J. Invest. Dermatol.* 97:291–297; Takahashi et al. (1993) *J. Biol. Chem.* 268:16443–16448).

Biosynthesis of the 15-HETE is better understood in terms of the enzymes involved. It is formed almost exclusively as the 15S enantiomer (Baer et al. (1991) *J. Lipid Research* 32:341–347; Baer et al. (1993) *J. Lipid Research* 34:1505–1514.) and its production can be accounted for by the 15S-lipoxygenases present in skin. Nugteren et al. (1987) *Biochim. Biophys. Acta* 921:135–141; Burrall et al. (1988) *J. Invest. Dermatol.* 4:294–297; Green, F. A. (1989) *J. Invest. Dermatol.* 93:486–491; Henneicke-von Zepelin et al. (1991) *J. Invest. Dermatol.* 97:291–297; Takahashi et al. (1993) *J. Biol. Chem.* 268:16443–16448; Baer et al. (1991) *J. Lipid Research* 32:341–347; Baer et al. (1993) *J. Lipid Research* 34:1505–1514; Zhao et al. (1995) *J. Lipid Res.* 36:24444–2449; Brash et al. (1997) *Proc. Natl. Acad Sci. USA* 94:6148–6152.

Formation of the 12-HETE in human skin is more complex, in that both 12R and 12S enantiomers are produced (Holtzman et al. (1989) *J. Clin. Invest.* 84:1446–1453; Henneicke-von Zepelin et al. (1991) *J. Invest. Dermatol.* 97:291–297; Baer et al. (1991) *J. Lipid Research* 32:341–347; Baer et al. (1993) *J. Lipid Research* 34:1505–1514. This is not mainly attributable to autoxidation as the proportions of 12R and 12S vary considerably and, aside from the 15S-HETE, comparable amounts of the other HETE regioisomers are not formed under the usual conditions of in vitro biosynthesis. Formation of the 12S-hydroxy enantiomer can be accounted for by the platelet-type of 12S-lipoxygenase that is a constituent of normal and inflammatory human skin (Hussain et al. (1994) *Am. J. Physiol.* 266:C243–C253; Takahashi et al. (1993) *J. Biol. Chem.* 268:16443–16448; Zhao et al. (1995) *J. Lipid Res.* 36:24444–2449; Brash et al. (1997) *Proc. Natl. Acad Sci. USA* 94:6148–6152). The enzyme or enzymes involved in the production of the-12R-enantiomer remain uncharacterized.

The first report of 12-HETE in human skin came in 1975, when Hammarström et al reported that the involved areas of epidermis in psoriasis have markedly increased concentrations of free arachidonic acid and 12-HETE (Hammarström et al. (1975) *Proc. Natl. Acad. Sci. USA* 72:5130–5134). Chiral analysis of the 12-HETE in psoriasis revealed that the major enantiomer is 12R-HETE (Woollard, P. M. (1986) *Biochem. Biophys. Res. Commun.* 136:169–175). It was shown subsequently that 12R-HETE is a prominent product in other non-psoriatic proliferative dermatoses (Baer et al. (1995) *J. Invest. Dermatol.* 104:251–255), and it is also formed in normal human skin as the minor 12-HETE enantiomer (Holtzman et al. (1989) *J. Clin. Invest.* 84:1446–1453; Baer et al. (1993) *J. Lipid Research* 34:1505–1514).

It has been questioned whether the enzyme responsible for the 12R-HETE synthesis is a cytochrome P450 or a lipoxygenase. The P450-catalyzed synthesis of 12R-HETE is precedented in rat and human liver microsomes and by purified cytochromes P450, as described in Capdevila et al. (1986) *Biochem. Biophys. Res. Commun.* 141:1007–1011; Oliw, E. H. (1993) *Biochim. Biophys. Acta* 1166:258–263; and Bylund et al. (1998) *J. Pharmacol. Exp. Ther.* 284:51–60. These well-defined P450 reactions are, however, associated with the formation of many additional products that are not typically formed in incubations of skin. The alternative pathway, via a 12R-lipoxygenase, is precedented in a marine invertebrate (Hawkins et al. (1987) *J. Biol. Chem.* 262:7629–7634; Hawkins et al. (1989) *FEBS Lett.* 247:9–12), but no R-lipoxygenase is known in mammals.

Therefore, what is needed, then, is further characterization of 12-lipoxygenase enzymes in vertebrates, particularly in mammals, and more particularly in humans. A novel isolated and purified 12R-lipoxygenase and a polynucleic acid encoding the same would have broad utility due to its role in arachidonic acid metabolism, a critical metabolic pathway.

DISCLOSURE OF THE INVENTION

The present invention contemplates an isolated and purified vertebrate lipoxygenase polypeptide which metabolizes arachidonic acid to 12R-hydroxyeicosatetraenoic acid (12R-HETE). More preferably, a polypeptide of the invention is a recombinant polypeptide. Even more preferably, a polypeptide of the present invention comprises a mammalian 12R-lipoxygenase (12R-LO). Even more preferably, a polypeptide of the present invention comprises a human 12R-LO. Even more preferably, a polypeptide of the present invention comprises the amino acid residue sequence of SEQ ID NO:2.

The present invention also provides an isolated and purified polynucleotide that encodes a lipoxygenase polypeptide which metabolizes arachidonic acid to 12R-HETE. In a preferred embodiment, a polynucleotide of the present invention comprises a DNA molecule from a vertebrate species. A preferred vertebrate is a mammal. A preferred mammal is a human. More preferably, a polynucleotide of the present invention encodes a polypeptide designated 12R-LO. Even more preferred, a polynucleotide of the present invention encodes a polypeptide comprising the amino acid residue sequence of SEQ ID NO:2. Most preferably, an isolated and purified polynucleotide of the invention comprises the nucleotide base sequence of SEQ ID NO:1.

In an alternative embodiment, the present invention provides an expression vector comprising a polynucleotide that encodes a vertebrate lipoxygenase polypeptide which metabolizes arachidonic acid to 12R-HETE. Also preferably, an expression vector of the present invention comprises a polynucleotide that encodes human 12R-LO. More preferably, an expression vector of the present invention comprises a polynucleotide that encodes a polypeptide comprising the amino acid residue sequence of SEQ ID NO:2. More preferably, an expression vector of the present invention comprises a polynucleotide comprising the nucleotide base sequence of SEQ ID NO:1. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes a vertebrate lipoxygenase polypeptide which metabolizes arachidonic acid to 12R-HETE. SEQ ID NO:1 and SEQ ID NO:2 set forth nucleotide and amino acid sequences from an exemplary vertebrate, human. Also contemplated by the present invention are homologous or biologically equivalent polynucleotides and lipoxygenase polypeptides found in other vertebrates. Preferably, a recombinant host cell of the present invention is transfected with the polynucleotide that encodes human 12R-LO. More preferably, a recombinant host cell of the present invention is transfected with the polynucleotide sequence of SEQ ID NO:1. Even more preferably, a host cell of the invention is a eukaryotic host cell. Still more preferably, a recombinant host cell of the present invention is a vertebrate cell. Preferably, a recombinant host cell of the invention is a mammalian cell.

In another aspect, a recombinant host cell of the present invention is a prokaryotic host cell. Preferably, a recombinant host cell of the invention is a bacterial cell, preferably a strain of *Escherichia coli*. More preferably, a recombinant host cell comprises a polynucleotide under the transcriptional control of regulatory signals functional in the recombinant host cell, wherein the regulatory signals appropriately control expression of the lipoxygenase polypeptide in a manner to enable all necessary transcriptional and post-transcriptional modification.

In yet another embodiment, the present invention contemplates a process of preparing a lipoxygenase polypeptide comprising transfecting a cell with polynucleotide that encodes a vertebrate lipoxygenase polypeptide which metabolizes arachidonic acid to 12R-HETE to produce a transformed host cell; and maintaining the transformed host cell under biological conditions sufficient for expression of the polypeptide. More preferably, the transformed host cell is a eukaryotic cell. More preferably still, the eukaryotic cell is a vertebrate cell. Alternatively, the host cell is a prokaryotic cell. More preferably, the prokaryotic cell is a bacterial cell of the DH5α strain of *Escherichia coli*. Even more preferably, a polynucleotide transfected into the transformed cell comprises the nucleotide base sequence of SEQ ID NO:1. SEQ ID NO:1 and SEQ ID NO:2 set forth nucleotide and amino acid sequences for an exemplary vertebrate, human. Also contemplated by the present invention are homologues or biologically equivalent lipoxygenase polynucleotides and polypeptides found in other vertebrates.

In still another embodiment, the present invention provides an antibody immunoreactive with a vertebrate lipoxygenase polypeptide which metabolizes arachidonic acid to 12R-HETE. SEQ ID NO:1 and SEQ ID NO:2 set forth nucleotide and amino acid sequences from an exemplary vertebrate, human. Also contemplated by the present invention are antibodies immunoreactive with homologues or biologically equivalent lipoxygenase polynucleotides and polypeptides found in other vertebrates. Preferably, an antibody of the invention is a monoclonal antibody. More preferably, the lipoxygenase polypeptide comprises human 12R-LO. Even more preferably, the lipoxygenase polypeptide comprises the amino acid residue sequence of SEQ ID NO:2.

In another aspect, the present invention contemplates a process of producing an antibody immunoreactive with a vertebrate lipoxygenase polypeptide which metabolizes arachidonic acid to 12R-HETE, the process comprising the steps of (a) transfecting a recombinant host cell with a polynucleotide that encodes a vertebrate lipoxygenase polypeptide which metabolizes arachidonic acid to 12R-HETE; (b) culturing the host cell under conditions sufficient for expression of the polypeptide; (c) recovering the polypeptide; and (d) preparing the antibody to the polypeptide. SEQ ID NO:1 and SEQ ID NO:2 set forth nucleotide and amino acid sequences from an exemplary vertebrate, human. Preferably, the host cell is transfected with the polynucleotide of SEQ ID NO:1. Even more preferably, the present invention provides an antibody prepared according to the process described above. Also contemplated by the present invention is the use of homologues or biologically equivalent polynucleotides and polypeptides found in other vertebrates to produce antibodies.

Alternatively, the present invention provides a process of detecting a vertebrate lipoxygenase polypeptide which metabolizes arachidonic acid to 12R-HETE, wherein the process comprises immunoreacting the polypeptide with an antibody prepared according to the process described above to form an antibody-polypeptide conjugate, and detecting the conjugate.

In yet another embodiment, the present invention contemplates a process of detecting a messenger RNA transcript that encodes a vertebrate lipoxygenase polypeptide which metabolizes arachidonic acid to 12R-HETE, wherein the process comprises hybridizing the messenger RNA transcript with a polynucleotide sequence that encodes that polypeptide to form a duplex; and detecting the duplex. Alternatively, the present invention provides a process of detecting a DNA molecule that encodes a vertebrate lipoxygenase polypeptide which metabolizes arachidonic acid to 12R-HETE, wherein the process comprises hybridizing DNA molecules with a polynucleotide that encodes a vertebrate lipoxygenase polypeptide which metabolizes arachidonic acid to 12R-HETE to form a duplex; and detecting the duplex.

In another aspect, the present invention contemplates a diagnostic assay kit for detecting the presence of a lipoxygenase polypeptide in a biological sample, where the kit comprises a first container containing a first antibody capable of immunoreacting with a vertebrate lipoxygenase polypeptide which metabolizes arachidonic acid to 12R-HETE, with the first antibody present in an amount sufficient to perform at least one assay. Preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support. More preferably still, the first and second antibodies comprise an indicator, and, preferably, the indicator is a radioactive label or an enzyme.

In an alternative aspect, the present invention provides a diagnostic assay kit for detecting the presence, in biological samples, of a lipoxygenase polypeptide, the kits comprising a first container that contains a second polynucleotide identical or complementary to a segment of at least 10 contiguous nucleotide bases of a polynucleotide that encodes a vertebrate lipoxygenase polypeptide which metabolizes arachidonic acid to 12R-HETE. Preferably, the polynucleotide encodes human 12R-LO.

In another embodiment, the present invention contemplates a diagnostic assay kit for detecting the presence, in a biological sample, of an antibody immunoreactive with a lipoxygenase polypeptide, the kit comprising a first container containing a vertebrate lipoxygenase polypeptide which metabolizes arachidonic acid to 12R-hydroxyeicosatetraenoic acid that immunoreacts with the antibody, with the polypeptide present in an amount sufficient to perform at least one assay. Preferably, the polypeptide comprises human 12R-LO.

Thus, a key aspect of this invention pertains to the discovery of a novel 12R-lipoxygenase (12R-LO) protein and nucleic acid encoding the 12R-LO protein. Preferred nucleic acid and amino acid sequences for 12R-LO are described in SEQ ID NO:1 and SEQ ID NO:2.

It is another aspect of this invention that the novel 12R-LO protein acts in the metabolism of arachidonic acid to 12-hydroxyeicosatetraenoic acid.

The foregoing aspects and embodiments have broad utility given the biological significance of the arachidonic acid pathway, as is known in the art. By way of example, the foregoing aspects and embodiments are useful in the preparation of screening assays and assay kits that are used to identify compounds that affect arachidonic acid metabolism, or that are used to detect the presence of the proteins and nucleic acids of this invention in biological samples. Additionally, it is well known that isolated and purified polypeptides have utility as feed additives for livestock and further polynucleotides encoding the polypeptides are thus useful in producing the polypeptides.

Following long-standing patent law convention, the terms "a" and "an" mean "one or more" when used in this application, including the claims.

Some of the aspects and objects of the invention having been stated hereinabove, other aspects and objects will become evident as the description proceeds, when taken in connection with the accompanying drawings as best described hereinbelow.

BRIEF DESCRIPTION OF THE DRAWINGS

FIG. 1 depicts analysis of deuterated 12-HETE formed in psoriatic scales.

FIGS. 2A–2E set forth cDNA (SEQ ID NO:1) and deduced amino acid (SEQ ID NO:2) sequences of the 12R-lipoxygenase of the present invention. Two actively expressing clones of the new cDNA were sequenced and were identical. Putative iron ligands are boxed. The extra 31 amino acids referred to hereinbelow are underlined. The cDNA sequence, including 5' and 3' UTR data, is set forth in the GenBank™/EMBL Data Bank with accession number AF038461.

FIG. 3 depicts expression in Hela cells and identification of the 12R-HETE product.

FIG. 4 depicts expression of the mRNA of the 12R-lipoxygenase of the present invention.

DETAILED DESCRIPTION OF THE INVENTION

Figure 1A:
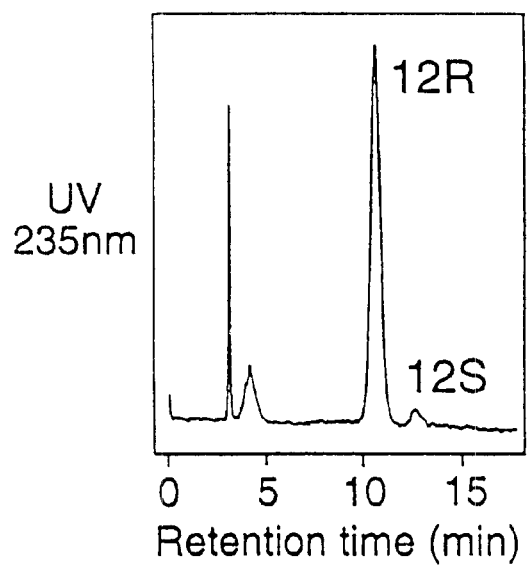
FIG. 1A depicts chiral HPLC of the deuterium-labeled 12-HETE from incubation of deuterated arachidonic acid in psoriatic scales. The 12-HETE was chromatographed as the PFB ester on a Chiralcel OD column using a solvent of hexane:isopropanol (100:5, v/v) and detected by UV monitoring at 235 nm.

A recognized feature of psoriasis and other proliferative dermatoses is accumulation in the skin of the unusual arachidonic acid metabolite, 12R-hydroxyeicosatetraenoic acid (12R-HETE). This hydroxy fatty acid is opposite in chirality to the product of the well known 12S-lipoxygenase and heretofore, in mammals, is known only as a product of cytochrome P450s. Mechanistic evidence for a lipoxygenase route to 12R-HETE in human psoriatic tissue is provided herein. A 12R-lipoxygenase that accounts for the biosynthesis is also described.

Initially, it is noted that the 12R-lipoxygenase of the present invention does not metabolize arachidonic acid directly to 12R-HETE. Rather, the 12R-lipoxygenase of the present invention metabolizes arachidonic acid to 12R-hydroperoxyeicosatetraenoic acid (12R-HPETE), which is then converted to 12R-HETE by commonly found peroxidase enzymes or by non-enzymatic reductants. As would thus be appreciated by one having ordinary skill in the art, when the phrase "metabolizes arachidonic acid to 12R-hydroxyeicosatetraenoic acid (12R-HETE)" is used herein and in the claims, it is meant to refer to and include the two-step process described above, i.e. that the 12R-lipoxygenase of the present invention metabolizes arachidonic acid to 12R-HPETE, which is then converted to 12R-HETE by commonly found peroxidase enzymes or by non-enzymatic reductants.

Applicants demonstrated retention of the C-12 deuterium of octadeuterated arachidonic acid in its conversion to 12R-HETE in incubations of psoriatic scales, indicating the end product is not formed by isomerization from 12S-H(P)ETE via the 12-keto derivative. Secondly, analysis of product formed from $[10_R-^3H]$- and $[10_S^3H]$-labeled arachidonic acids revealed that 12R-HETE synthesis is associated with stereospecific removal of the pro-R hydrogen from the 10-carbon of arachidonate. This result is compatible with 12R-lipoxygenase-catalyzed formation of 12R-HETE and not with a P450-catalyzed route to 12R-HETE in psoriatic scales.

Applicants then cloned a new lipoxygenase from human keratinocytes wherein the cDNA and deduced amino acid sequences share ≦50% identity to other human lipoxygenases. This enzyme, when expressed in Hela cells, oxygenates arachidonic acid to 12-H(P)ETE, 98% 12R in configuration. The 12R-lipoxygenase cDNA is detectable by PCR in psoriatic scales and as a 2.5 kb mRNA by Northern analysis of keratinocytes. Identification of this enzyme extends the known distribution of R-lipoxygenases to vertebrates, particularly to mammals, and more particularly to humans, and presents a new target for therapeutic interventions in psoriasis.

Definitions and Techniques Affecting Gene Products and Genes

The present invention concerns DNA segments, isolatable from vertebrate tissue, preferably from mammalian tissue, and more preferably from human tissue, which are free from genomic DNA and which are capable of conferring arachidonic acid metabolism activity in a recombinant host cell when incorporated into the recombinant host cell. As used herein, the term "mammalian tissue" refers to, among others, normal mammalian epithelial tissues, as exemplified by, but not limited to, human keratinocytes and to abnormal mammalian epithelial tissues, as exemplified by, but not limited to, psoriatic scales. DNA segments capable of conferring arachidonic acid metabolism activity may encode complete lipoxygenase polypeptides, cleavage products and biologically actively functional domains thereof.

The terms "lipoxygenase polypeptide", "lipoxygenase gene product", "lipoxygenase", "LO", "12R-LO gene product", and "12R-LO", as used in the specification and in the claims refer to proteins having amino acid sequences which are substantially identical to the respective native lipoxygenase amino acid sequences and which are biologically active in that they are capable of reacting with arachidonic acid or are capable of cross-reacting with an anti-LO antibody raised against a lipoxygenase, such as 12R-LO. Such sequences are disclosed herein. The terms "lipoxygenase polypeptide", "lipoxygenase gene product", "lipoxygenase", "Lox", "12R-LO gene product", and "12R-LO" also include analogs of lipoxygenase molecules which exhibit at least some biological activity in common with native lipoxygenase, 12R-LO. Furthermore, those skilled in the art of mutagenesis will appreciate that other analogs, as yet undisclosed or undiscovered, may be used to construct lipoxygenase analogs. There is no need for a "lipoxygenase polypeptide", "lipoxygenase" or "LO", or a "12R-LO" to comprise all, or substantially all, of the amino acid sequence of the native lipoxygenase genes. Shorter or longer sequences are anticipated to be of use in the invention.

The terms "lipoxygenase gene" and "12R-LO gene" refer to any DNA sequence that is substantially identical to a DNA sequence encoding a lipoxygenase or 12R-LO as defined above. The terms also refer to RNA, or antisense sequences, compatible with such DNA sequences. A "lipoxygenase gene" or a "12R-LO gene" may also comprise any combination of associated control sequences.

The term "substantially identical", when used to define either a lipoxygenase or 12R-LO amino acid sequence, or a lipoxygenase or 12R-LO nucleic acid sequence, means that a particular sequence, for example, a mutant sequence, varies from the sequence of a natural lipoxygenase, 12R-LO, by one or more deletions, substitutions, or additions, the net effect of which is to retain at least some of biological activity of the lipoxygenase or the 12R-LO protein. Alternatively, DNA analog sequences are "substantially identical" to specific DNA sequences disclosed herein if: (a) the DNA analog sequence is derived from coding regions of the natural lipoxygenase or 12R-LO gene; or (b) the DNA analog sequence is capable of hybridization of DNA sequences of (a) under moderately stringent conditions and which encode biologically active lipoxygenase or 12R-LO gene; or (c) the DNA sequences are degenerative as a result of the genetic code to the DNA analog sequences defined in (a) and/or (b). Substantially identical analog proteins will be greater than about 60% identical to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences.

Percent Similarity

Percent similarity may be determined, for example, by comparing sequence information using the GAP computer program, available from the University of Wisconsin Geneticist Computer Group. The GAP program utilizes the alignment method of Needleman et al. 1970, as revised by Smith et al. 1981. Briefly, the GAP program defines similarity as the number of aligned symbols (i.e. nucleotides or amino acids) which are similar, divided by the total number of symbols in the shorter of the two sequences. The preferred default parameters for the GAP program include: (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps.

The term "homology" describes a mathematically based comparison of sequence similarities which is used to identify genes or proteins with similar functions or motifs. Accordingly, the term "homology" is synonymous with the term "similarity" and "percent similarity" as defined above. Thus, the phrases "substantial homology" or "substantial similarity" have similar meanings.

Nucleic Acid Sequences

In certain embodiments, the invention concerns the use of lipoxygenase genes and gene products, such as the 12R-LO gene product, that include within their respective sequences a sequence which is essentially that of a lipoxygenase or 12R-LO gene, or the corresponding proteins. The term "a sequence essentially as that of lipoxygenase or 12R-LO gene or gene product", means that the sequence substantially corresponds to a portion of a lipoxygenase or 12R-LO gene or gene product and has relatively few bases or amino acids (whether DNA or protein) which are not identical to those of a lipoxygenase or 12R-LO gene or gene product, (or a biologically functional equivalent of, when referring to proteins). The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of a lipoxygenase or 12R-LO gene or gene product, will be sequences which are "essentially the same".

Lipoxygenase and 12R-LO genes which have functionally equivalent codons are also covered by the invention. The term "functionally equivalent codon" is used herein to refer to codons that encode the same amino acid, such as the six codons for arginine or serine, and also to refer to codons that encode biologically equivalent amino acids (see Table 1).

TABLE 1

Functionally Equivalent Codons.

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glumatic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments which are complementary, or essentially complementary, to the sequences set forth in the specification. Nucleic acid sequences which are "complementary" are those which are base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment in question under relatively stringent conditions such as those described herein. A particular example of a contemplated complementary nucleic acid segment is an antisense oligonucleotide.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. (See, e.g., Wetmur & Davidson, 1968).

Probe sequences may also hybridize specifically to duplex DNA under certain conditions to form triplex or other higher order DNA complexes. The preparation of such probes and suitable hybridization conditions are well known in the art.

As used herein, the term "DNA segment" refers to a DNA molecule which has been isolated free of total genomic DNA of a particular species. Furthermore, a DNA segment encoding a lipoxygenase or 12R-LO gene product refers to a DNA segment which contains lipoxygenase or 12R-LO coding sequences, yet is isolated away from, or purified free from, total genomic DNA of Homo sapiens. Included within the term "DNA segment" are DNA segments and smaller fragments of such segments, and also recombinant vectors, including, for example, plasmids, cosmids, phages, viruses, and the like.

Similarly, a DNA segment comprising an isolated or purified lipoxygenase or 12R-LO gene refers to a DNA segment including lipoxygenase or 12R-LO coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, the lipoxygenase or 12R-LO gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode a 12R-LO protein that includes within its amino acid sequence the amino acid sequence of SEQ ID NO:2. In other particular embodiments, the invention concerns isolated DNA segments and recombinant vectors incorporating DNA sequences which encode a protein that includes within its amino acid sequence the amino acid sequence of the 12R-LO protein corresponding to human keratinocytes.

It will also be understood that this invention is not limited to the particular nucleic acid and amino acid sequences of SEQ ID NOS:1 and 2. Recombinant vectors and isolated DNA segments may therefore variously include the 12R-LO encoding region itself, include coding regions bearing selected alterations or modifications in the basic coding region, or include encoded larger polypeptides which nevertheless include 12R-LO encoding regions or may encode biologically functional equivalent proteins or peptides which have variant amino acid sequences.

In certain embodiments, the invention concerns isolated DNA segments and recombinant vectors which encode a protein or peptide that includes within its amino acid sequence an amino acid sequence essentially as set forth in SEQ ID NO:2. Naturally, where the DNA segment or vector encodes a full length 12R-LO gene product, the most preferred sequence is that which is essentially as set forth in SEQ ID NO:1 and which encode a protein that exhibits arachidonic acid reactivity in human keratinocytes, as may be determined by HPLC analysis, as disclosed herein.

The term "a sequence essentially as set forth in SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined in detail herein. Accordingly, sequences, which have between about 70% and about 80%; or more preferably, between about 81% and about 90%; or even more preferably, between about 91% and about 99%; of amino acids which are identical or functionally equivalent to the amino acids of SEQ ID NO:2, will be sequences which are "essentially as set forth in SEQ ID NO:2".

In particular embodiments, the invention concerns gene therapy methods that use isolated DNA segments and recombinant vectors incorporating DNA sequences which encode a protein that includes within its amino acid sequence an amino acid sequence in accordance with SEQ ID NO:2, SEQ ID NO:2 being derived from keratinocytes from Homo sapiens. In other particular embodiments the invention concerns isolated DNA sequences and recombinant DNA vectors incorporating DNA sequences which encode a protein that includes within its amino acid sequence the amino acid sequence of the 12R-LO protein from human keratinocytes.

In certain other embodiments, the invention concerns isolated DNA segments and recombinant vectors that include within their sequence a nucleic acid sequence essentially as set forth in SEQ ID NO:1. The term "essentially as set forth in SEQ ID NO:1" is used in the same sense as described above and means that the nucleic acid sequence substantially corresponds to a portion of SEQ ID NO:1, respectively, and has relatively few codons which are not identical, or functionally equivalent, to the codons of SEQ ID NO:1, respectively. Again, DNA segments which encode gene products exhibiting arachidonic acid metabolism activity of the 12R-LO gene product will be most preferred. The term "functionally equivalent codon" is used herein to refer to codons that encode the same amino acid, such as the six codons for arginine or serine, and also to refer to codons that encode biologically equivalent amino acids (see Table 1).

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1, such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

The DNA segments of the present invention encompass biologically functional equivalent 12R-LO proteins and peptides. Such sequences may rise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test 12R-LO mutants in order to examine arachidonic acid reactivity at the molecular level.

If desired, one may also prepare fusion proteins and peptides, e.g., where the 12R-LO coding region is aligned within the same expression unit with other proteins or peptides having desired functions, such as for purification or immunodetection purposes (e.g., proteins which may be purified by affinity chromatography and enzyme label coding regions, respectively).

Recombinant vectors form important further aspects of the present invention. Particularly useful vectors are contemplated to be those vectors in which the coding portion of the DNA segment is positioned under the control of a promoter. The promoter may be in the form of the promoter which is naturally associated with the 12R-LO gene, e.g., in keratinocytes, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a 12R-LO gene in its natural environment. Such promoters may include promoters isolated from bacterial, viral, eukaryotic, or mammalian cells.

Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al., 1989, specifically incorporated herein by reference. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the vaccina virus promoter and the baculovirus promoter, which are more fully described below.

As mentioned above, in connection with expression embodiments to prepare recombinant 12R-LO proteins and peptides, it is contemplated that longer DNA segments will most often be used, with DNA segments encoding the entire 12R-LO protein, functional domains or cleavage products thereof, being most preferred. However, it will be appreciated that the use of shorter DNA segments to direct the expression of 12R-LO peptides or epitopic core regions, such as may be used to generate anti-12R-LO antibodies, also falls within the scope of the invention.

DNA segments which encode peptide antigens from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides. DNA segments encoding full length proteins may have a minimum coding length on the order of about 2,500 nucleotides for a protein in accordance with SEQ ID NO:2.

Naturally, the present invention also encompasses DNA segments which are complementary, or essentially complementary, to the sequence set forth in SEQ ID NO:1. The terms "complementary" and "essentially complementary" are defined above. Excepting intronic or flanking regions, and allowing for the degeneracy of the genetic code, sequences which have between about 70% and about 80%; or more preferably, between about 81% and about 90%; or even more preferably, between about 91% and about 99%; of nucleotides which are identical or functionally equivalent (i.e. encoding the same amino acid) of nucleotides of SEQ ID NO:1, will be sequences which are "essentially as set forth in SEQ ID NO:1". Sequences which are essentially the same as those set forth in SEQ ID NO:1 may also be functionally defined as sequences which are capable of hybridizing to a nucleic acid segment containing the complement of SEQ ID NO:1 under relatively stringent conditions. Suitable relatively stringent hybridization conditions are described herein and will be well known to those of skill in the art.

Biologically Functional Equivalents

As mentioned above, modification and changes may be made in the structure of the lipoxygenase proteins and peptides, including 12R-LO, described herein and still obtain a molecule having like or otherwise desirable characteristics. For example, certain amino acids may be substituted for other amino acids in a protein structure without appreciable loss of interactive capacity with structures such as, for example, C-10 carbon of arachidonic acid. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of the lipoxygenase proteins and peptides, including 12R-LO, (or underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention, where if any changes, for example, in an iron binding-moiety of 12R-LO that render the peptide incapable of metabolism of arachidonic acid to 12R-hydroxyeicosatetraenoic acid would result in a loss of utility of the resulting peptide for the present invention.

Amino acid substitutions, such as those which might be employed in modifying the lipoxygenase proteins and peptides, including 12R-LO, described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA, taking into consideration also that the genetic code is degenerate and that two or more codons may code for the same amino acid.

Sequence Modification Techniques

Modifications to the lipoxygenase proteins and peptides, including 12R-LO, described herein may be carried out using techniques such as site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 30 nucleotides in length is preferred, with about 5 to 10 residues on both sides of the junction of the sequence being altered.

In general, the technique of site-specific mutagenesis is well known in the art as exemplified by publications (e.g., Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes, for example, the 12R-LO gene. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected gene using site-directed mutagenesis is provided as a means of producing potentially useful 12R-LO or other arachidonic acid metabolizing species and is not meant to be limiting as there are other ways in which sequence variants of these peptides may be obtained. For example, recombinant vectors encoding the desired genes may be treated with mutagenic agents to obtain sequence variants (see, e.g., a method described by Eichenlaub, 1979) for the mutagenesis of plasmid DNA using hydroxylamine.

Other Structural Equivalents

In addition to the lipoxygenase peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

Introduction of Gene Products

Where the gene itself is employed to introduce the gene products, a convenient method of introduction will be through the use of a recombinant vector which incorporates the desired gene, together with its associated control sequences. The preparation of recombinant vectors is well known to those of skill in the art and described in many references, such as, for example, Sambrook et al. (1989), specifically incorporated herein by reference.

In vectors, it is understood that the DNA coding sequences to be expressed, in this case those encoding the lipoxygenase gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One may also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While use of the control sequences of the specific gene (i.e., the 12R-LO promoter for 12R-LO) will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothionein promoter, and the like.

As is known in the art, a promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

For introduction of, for example, the 12R-LO gene, it is proposed that one will desire to preferably employ a vector construct that will deliver the desired gene to the affected cells. This will, of course, generally require that the construct be delivered to the targeted cells, for example, keratinocytes. It is proposed that this may be achieved most preferably by introduction of the desired gene through the use of a viral vector to carry the 12R-LO sequence to efficiently infect the cells. These vectors will preferably be an adenoviral, a retroviral, a vaccinia viral vector or adeno-associated virus. These vectors are preferred because they have been successfully used to deliver desired sequences to cells and tend to have a high infection efficiency.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Where the 12R-LO gene itself is employed it will be most convenient to simply use the wild type 12R-LO gene directly. However, it is contemplated that certain regions of the 12R-LO gene may be employed exclusively without employing the entire wild type 12R-LO gene. It is proposed that it will ultimately be preferable to employ the smallest region needed to regulate the metabolism of arachidonic acid to 12R-HETE so that one is not introducing unnecessary DNA into cells which receive either a 12R-LO gene construct. Techniques well known to those of skill in the art, such as the use of restriction enzymes, will allow for the generation of small regions of the 12R-LO gene. The ability of these regions to regulate the metabolism of arachidonic acid to 12R-HETE can easily be determined by the assays reported in the Examples. In general, techniques for assessing metabolism of arachidonic acid to 12R-HETE are well known in the art.

It is also contemplated to be within the scope of the present invention to prepare a transgenic non-human animal which expresses the 12R-LO gene of the present invention. Preferably, the preparation of a transgenic animal which overexpresses human 12R-LO in the skin of the animal to establish a psoriasis-like disorder in the animal is contemplated to be within the scope of the present invention. A preferred transgenic animal is a mouse.

Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); 5,162,215 (transgenic avian species) and U.S. Pat. No. 5,741,957 (transgenic bovine species), the entire contents of each of which are herein incorporated by reference.

With respect to an exemplary method for the preparation of a transgenic mouse, cloned recombinant or synthetic DNA sequences or DNA segments encoding 12R-LO are injected into fertilized mouse eggs. The injected eggs are implanted in pseudo pregnant females and are grown to term to provide transgenic mice whose cells express 12R-LO. The injected sequences are constructed having promoter sequences connected so as to express the desired protein in skin tissues of the transgenic mouse.

As noted above, a recognized feature of psoriasis and other proliferative dermatoses is accumulation in the skin of the unusual arachidonic acid metabolite, 12R-HETE. Thus, the inhibition of the accumulation in the skin of 12R-HETE is desirable in the treatment of psoriasis and other proliferative dermatoses. Accordingly, the transgenic mice provide useful models for studying compounds being tested for their usefulness in treating psoriasis and other proliferative dermatoses.

Generation of Antibodies

In still another embodiment, the present invention provides an antibody immunoreactive with a polypeptide of the present invention. Preferably, an antibody of the invention is a monoclonal antibody. Means for preparing and characterizing antibodies are well known in the art (See, e.g., *Antibodies A Laboratory Manual*, E. Howell and D. Lane, Cold Spring Harbor Laboratory, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogencity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention contemplates a process of producing an antibody immunoreactive with a lipoxygenase polypeptide, such as 12R-LO, the process comprising the steps of (a) transfecting recombinant host cells with a polynucleotide that encodes that polypeptide; (b) culturing the host cells under conditions sufficient for expression of the polypeptide; (c) recovering the polypeptide; and (d) preparing antibodies to the polypeptide. Preferably, the lipoxygenase polypeptide is capable of metabolizing arachidonic acid. Even more preferably, the present invention provides antibodies prepared according to the process described above.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 mg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5\times10^7$ to $2\times10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immuno-specific reaction with the bound antibody. The polypeptide or polynucleotide is then easily removed from the substrate and purified.

Detecting a Polynucleotide or a Polypeptide of the Present Invention

Alternatively, the present invention provides a process of detecting a polypeptide of the present invention, wherein the process comprises immunoreacting the polypeptides with antibodies prepared according to the process described above to form antibody-polypeptide conjugates, and detecting the conjugates.

In yet another embodiment, the present invention contemplates a process of detecting messenger RNA transcripts that encode a polypeptide of the present invention, wherein the process comprises hybridizing the messenger RNA transcripts with polynucleotide sequences that encode the polypeptide to form duplexes; and detecting the duplex. Alternatively, the present invention provides a process of detecting DNA molecules that encode a polypeptide of the present invention, wherein the process comprises hybridizing DNA molecules with a polynucleotide that encodes that polypeptide to form duplexes; and detecting the duplexes.

Screening Assays

In yet another aspect, the present invention contemplates a process of screening substances for their ability to affect arachidonic acid metabolism. Utilizing the methods and compositions of the present invention, screening assays for the testing of candidate substances can be derived. A candidate substance is a substance which potentially can promote or inhibit arachidonic acid metabolism, by binding or other intramolecular interaction, with a lipoxygenase polypeptide, such as 12R-LO, that metabolizes arachidonic acid. As noted above, a recognized feature of psoriasis and other proliferative dermatoses is accumulation in the skin of the unusual arachidonic acid metabolite, 12R-hydroxyeicosatetraenoic acid (12R-HETE). Thus, a candidate substance identified according to the screening assay described herein is contemplated to have the ability to inhibit accumulation in the skin of 12R-HETE, and thus have utility in the treatment of psoriasis and other proliferative dermatoses.

An exemplary method of screening candidate substances for their ability to modulate arachidonic acid metabolism comprises the steps of: (a) establishing replicate test and control samples that comprise arachidonic acid and a vertebrate lipoxygenase polypeptide capable of converting arachidonic acid to 12R-hydroxyeicosatetraenoic acid; (b) administering a candidate substance to test sample but not the control sample; (c) measuring 12R-hydroxyeicosatetraenoic acid levels in the test and the control samples; and (d) determining that the candidate compound modulates arachidonic acid metabolism if the 12R-hydroxyeicosatetraenoic acid level measured for the test sample is greater or less than the 12R-hydroxyeicosatetraenoic acid level measured for the control sample. The replicate test and control samples can further comprise a cell that expresses a vertebrate lipoxygenase polypeptide capable of converting arachidonic acid to 12R-hydroxyeicosatetraenoic acid. The present invention also contemplates a recombinant cell line suitable for use in the exemplary method.

Thus, a screening assay of the present invention generally involves determining the ability of a candidate substance to affect metabolism of arachidonic acid in a target cell, such as the screening of candidate substances to identify those that modulate, i.e. inhibit or promote, metabolism of arachidonic acid. Target cells can be either naturally occurring cells known to contain a polypeptide of the present invention or transformed cell produced in accordance with a process of transformation set forth hereinbefore.

As is well known in the art, a screening assay provides a cell under conditions suitable for testing'arachidonic acid metabolism. These conditions include but are not limited to pH, temperature, tonicity, the presence of relevant factors involved in arachidonic acid metabolism (e.g., metal ions such as for example $Ca^{++}$, growth factor, interleukins, or colony stimulating factors), and relevant modifications to the polypeptide such as glycosylation or prenylation. It is contemplated that a polypeptide of the present invention can be expressed and utilized in a prokaryotic or eukaryotic cell. The host cell can also be fractionated into sub-cellular fractions where the receptor can be found. For example, cells expressing the polypeptide can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of factors can be required for the proper testing of arachidonic acid metabolism in specific cells. Such factors include, for example, the presence and absence (withdrawal) of growth factor, interleukins, or colony stimulating factors. U.S. Pat. No. 5,645,999 also describes exemplary screening assays, and the entire contents of U.S. Pat. No. 5,645,999 are herein incorporated by reference.

In one embodiment, a screening assay is designed to be capable of discriminating candidate substances having selective ability to interact with one or more of the polypeptides of the present invention but which polypeptides are without a substantially overlapping activity with another of those polypeptides identified herein.

Many substances which promote or inhibit the activity of the other human lipoxygenases have been identified, and thus represent suitable candidate substances for a screening assay as described above. For example, the 5S-lipoxygenase inhibitor zileuton is commerically available from Abbot Laboratories, Abbot Park, Ill. and is marketed as a treatment for asthma. Additionally, suitable candidate substances may comprise compositions which inhibit the activity of the known 12S-lipoxygenase, such as those described in U.S. Pat. No. 5,326,902 issued to Seipp et al. on Jul. 5, 1994, U.S. Pat. No. 5,234,933 issued to Marnett et al. on Aug. 10, 1993, and PCT Publication WO 93125521 of Johnson et al. published Dec. 23, 1993. Additional screening assay techniques are described in the these references, and hence, the entire contents of the these references are incorporated herein by reference. Other examples of candidate substances would be apparent to those having ordinary skill in the art.

Therapeutic Methods

A therapeutic method is contemplated according to the present invention. Such a method may comprise promoting or inhibiting 12R-LO in a vertebrate by administering an effective amount of a substance that inhibits or promotes expression of a 12R-LO-encoding nucleic acid segment in the vertebrate. Examples of such a substance, include, for example, an antisense oligonucleotide derived from SEQ ID NO:1. Therapeutic methods utilizing antisense oligonucleotides have been described in the art, for example in U.S. Pat. Nos. 5,627,158 and 5,734,033, the contents of each of which are herein incorporated by reference.

The therapeutic method may also comprise a substance that inhibits or promotes metabolism of arachidonic acid by inhibiting or promoting the activity of 12R-LO. Such a substance may be identified according to the screening assay set forth above. A preferred example of a vertebrate is a mammal. A preferred example of a mammal is a human. Thus, the method may comprise treating a patient suffering from a disorder associated with the metabolism of arachidonic acid by 12R-LO by administering to the patient an effective 12R-LO modulating amount of a substance identified according to the screening assay described above. By the term "modulating", it is contemplated that the substance can either promote or inhibit the activity of 12R-LO, depending on the disorder to be treated.

As noted above, a recognized feature of psoriasis and other proliferative dermatoses is accumulation in the skin of the unusual arachidonic acid metabolite, 12R-hydroxyeicosatetraenoic acid (12R-HETE). Thus, the inhibition of the accumulation in the skin of 12R-HETE is desirable in the treatment of psoriasis and other proliferative dermatoses. Accordingly, as a preferred example, the contemplated therapeutic method comprises treating a patient suffering from psoriasis by administering to the patient an effective 12R-LO inhibiting amount of a substance identified according to the screening assay described above. Alternatively, the contemplated therapeutic method comprises treating a patient suffering from psoriasis by administering an effective amount of a substance that inhibits or promotes expression of a 12R-LO-encoding nucleic acid segment in the patient. Such a substance may comprise, for example, an antisense oligonucleotide derived from SEQ ID NO:1.

The 12R-LO modulating substance and the substance that inhibits or promotes expression of a 12R-LO-encoding nucleic acid segment are thus adapted for administration as a pharmaceutical composition. Formulation and dose preparation techniques have been described in the art, see for example, those described in U.S. Pat. No. 5,326,902 issued to Seipp et al. on Jul. 5, 1994, U.S. Pat. No. 5,234,933 issued to Marnett et al. on Aug. 10, 1993, and PCT Publication WO 93/25521 of Johnson et al. published Dec. 23, 1993, the entire contents of each of which are herein incorporated by reference.

For the purposes described above, the identified substances may normally be administered systemically or partially, usually by oral or parenteral administration. The doses to be administered are determined depending upon age, body weight, symptom, the desired therapeutic effect, the route of administration, and the duration of the treatment etc. In a human adult, the doses per person per administration are generally between 1 mg and 500 mg, by oral administration, up to several times per day, and between 1 mg and 100 mg, by parenteral administration up to several times per day. Since the doses to be used depend upon various conditions, as mentioned above, there may be a case in which doses are lower than or greater than the ranges specified above.

Solid compositions for oral administration include compressed tablets, pills, dispersible powders, capsules, and granules. In such compositions, one or more of the active substance(s) is or are, admixed with at least one inert diluent (lactose, mannitol, glucose, hydroxypropylcellulose, microcrystalline cellulose, starch, polyvinylpyrrolidone, magnesium metasilicate alminate, etc.). The compositions may also comprise, as is normal practice, additional substances other than inert diluents: e.g. lubricating agents (magnesium stearate, etc.), disintegrating agents (cellulose, calcium glycolate etc.), and assisting agent for dissolving (glutamic acid, aspartic acid, etc.) stabilizing agent (lactose etc.). The tablets or pills may, if desired, be coated with gastric or enteric material (sugar, gelatin, hydroxypropylcellulose or hydroxypropylmethyl cellulose phthalate, etc.). Capsules include soft ones and hard ones.

Liquid compositions for oral administration include pharmaceutically-acceptable emulsions, solutions, suspensions, syrups and elixirs. In such compositions, one or more of the active substance(s) is or are admixed with inert diluent(s) commonly used in the art (purified water, ethanol etc.). Besides inert diluents, such compositions may also comprise adjuvants (wetting agents, suspending agents, etc.), sweetening agents, flavoring agents, perfuming agents and preserving agents.

Other compositions for oral administration include spray compositions which may be prepared by known methods and which comprise one or more of the active substance(s). Spray compositions may comprise additional substances other than inert diluents: e.g. preserving agents (sodium sulfite, etc.), isotonic buffer (sodium chloride, sodium citrate, citric acid, etc.). For preparation of such spray compositions, for example, the method described in U.S. Pat. Nos. 2,868,691 or 3,095,355 may be used.

Injections for parenteral administration include sterile aqueous or non-aqueous solution, suspensions and emulsions. In such compositions, one or more of active substance (s) is or are admixed with at least one inert aqueous diluent(s) (distilled water for injection, physiological salt solution etc.) or inert non-aqueous diluent(s) (propylene glycol, polyethylene glycol, olive oil, ethanol, POLYSOL-BATE 80 (registered trade mark) etc.). Injections may comprise additional other than inert diluents: e.g. preserving agents, wetting agents, emulsifying agents, dispersing agents, stabilizing agents (lactose, etc.), assisting agents such as for dissolving (glutamic acid, aspartic acid, etc.). They may be sterilized, for example, by filtration through a bacteria-retaining filter, by incorporation of sterilizing agents in the compositions or by irradiation. They also be manufactured in the form of sterile solid compositions, for example, by freeze-drying, and which can be dissolved in sterile water or some other sterile diluents for injection immediately before use.

Other compositions for administration include liquids for external use, and endermic linaments (ointment, etc.), suppositories and pessaries which comprise one or more of the active substance(s) and may be prepared by known methods.

Screening Assays for a Polypeptide of the Present Invention

The present invention provides a process of screening a biological sample for the presence of a lipoxygenase polypeptide, such as 12R-LO. Preferably, the lipoxygenase polypeptide reacts with arachidonic acid. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay process, a biological sample is exposed to an antibody immunoreactive with the polypeptide whose presence is being assayed. Typically, exposure is accomplished by forming an admixture in a liquid medium that contains both the antibody and the candidate polypeptide. Either the antibody or the sample with the polypeptide can be affixed to a solid support (e.g., a column or a microtiter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the polypeptide.

Exposure time will vary inter alia with the biological conditions used, the concentration of antibody and polypeptide and the nature of the sample (e.g., fluid or tissue sample). Means for determining exposure time are well known to one of ordinary skill in the art. Typically, where the sample is fluid and the concentration of polypeptide in that sample is about $10^{-10}$M, exposure time is from about 10 minutes to about 200 minutes.

The presence of polypeptide in the sample is detected by detecting the formation and presence of antibody-polypeptide conjugates. Means for detecting such antibody-antigen (e.g., receptor polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}P$, $^{125}I$, $^{14}C$), a second antibody or an enzyme such as horse radish peroxidase. Means for affixing indicators to antibodies are well known in the art. Commercial kits are available.

Screening Assay for Anti-Polypeptide Antibody

In another aspect, the present invention provides a process of screening a biological sample for the presence of antibodies immunoreactive with a lipoxygenase polypeptide, such as 12R-LO. Preferably the lipoxygenase polypeptide reacts with arachidonic acid. In accordance with such a process, a biological sample is exposed to a lipoxygenase polypeptide, such as 12R-LO, under biological conditions and for a period of time sufficient for antibody-polypeptide conjugate formation and the formed conjugates are detected.

Screening Assay for Polynucleotide That Encodes a Lipoxygenase Polypeptide of the Present Invention A DNA molecule and, particularly a probe molecule, can be used for hybridizing as an oligonucleotide probe to a DNA source suspected of encoding a lipoxygenase polypeptide of the present invention, such as 12R-LO. Preferably the lipoxygenase polypeptide reacts with arachidonic acid. The probing is usually accomplished by hybridizing the oligonucleotide to a DNA source suspected of possessing a lipoxygenase gene. In some cases, the probes constitute only a single probe, and in others, the probes constitute a collection of probes based on a certain amino acid sequence or sequences of the polypeptide and account in their diversity for the redundancy inherent in the genetic code.

A suitable source of DNA for probing in this manner is capable of expressing a polypeptide of the present invention and can be a genomic library of a cell line of interest. Alternatively, a source of DNA can include total DNA from the cell line of interest. Once the hybridization process of the invention has identified a candidate DNA segment, one confirms that a positive clone has been obtained by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) means for detecting and isolating other members of the polypeptide family and related polypeptides from a DNA library potentially containing such sequences; (3) primers for hybridizing to related sequences for the purpose of amplifying those sequences; (4) primers for altering native lipoxygenase DNA sequences; as well as other techniques which rely on the similarity of the DNA sequences to those of the DNA segments herein disclosed.

As set forth above, in certain aspects, DNA sequence information provided by the invention allows for the preparation of relatively short DNA (or RNA) sequences (e.g., probes) that specifically hybridize to encoding sequences of a selected lipoxygenase gene. In these aspects, nucleic acid probes of an appropriate length are prepared based on a consideration of the encoding sequence for a polypeptide of this invention. The ability of such nucleic acid probes to specifically hybridize to other encoding sequences lend them particular utility in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of a nucleic acid sequence of the present invention, such as that shown in SEQ ID NO:1. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments can be readily prepared by, for example, directly synthesizing the fragment by chemical means, by application of nucleic acid reproduction technology, such as the PCR technology of U.S. Pat. No. 4,683,202, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M NaCl at temperatures of 50° C. to 70° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate polypeptide coding sequences from related species, functional equivalents, or the like, less stringent hybridization conditions are typically needed to allow formation of the heteroduplex. Under such circumstances, one employs conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Assay Kits

In another aspect, the present invention contemplates diagnostic assay kits for detecting the presence of a polypeptide of the present invention in biological samples, where the kits comprise a first container containing a first antibody capable of immunoreacting with the polypeptide, with the first antibody present in an amount sufficient to perform at least one assay. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The present invention also contemplates a diagnostic kit for screening agents. Such a kit can contain a polypeptide of the present invention. The kit can contain reagents for detecting an interaction between an agent and a receptor of the present invention. The provided reagent can be radiolabelled. The kit can contain a known radiolabelled agent capable of binding or interacting with a receptor of the present invention.

In an alternative aspect, the present invention provides diagnostic assay kits for detecting the presence, in biological samples, of a polynucleotide that encodes a polypeptide of the present invention, the kits comprising a first container that contains a second polynucleotide identical or complementary to a segment of at least 10 contiguous nucleotide bases of, as a preferred example, SEQ ID NO:1.

In another embodiment, the present invention contemplates diagnostic assay kits for detecting the presence, in a biological sample, of antibodies immunoreactive with a polypeptide of the present invention, the kits comprising a first container containing a lipoxygenase polypeptide, such as 12R-LO, that immunoreacts with the antibodies, with the polypeptide present in an amount sufficient to perform at least one assay. Preferably, the lipoxygenase polypeptide metabolizes arachidonic acid. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media or a microscope slide. When the reagent provided is a dry powder, the powder can be reconstituted by the addition of a suitable solvent. The solvent can be provided.

The following examples have been included to illustrate preferred modes of the invention. Certain aspects of the following examples are described in terms of techniques and procedures found or contemplated by the present inventors to work well in the practice of the invention. These examples are exemplified through the use of standard laboratory practices of the inventors. In light of the present disclosure and the general level of skill in the art, those of skill will appreciate that the following examples are intended to be exemplary only and that numerous changes, modifications and alterations can be employed without departing from the spirit and scope of the invention.

EXAMPLE 1

In this Example mechanistic evidence is presented that is compatible only with a lipoxygenase pathway to 12R-HETE in human psoriatic skin. The cloning and initial characterization of a 12R-lipoxygenase from normal human keratinocytes is also described, thus establishing the existence of R-lipoxygenases beyond the invertebrate world.

Experimental Procedures

Materials - [1-$^{14}$C]Arachidonic acid was purchased from NEN (Dupont). [5,6,8,9,11,12,14,15- $^2$H$_8$]Arachidonic acid was from a batch prepared as previously described (Taber et al. (1982) *Methods Enzymol.* 86:366–369); $^2$H$_8$ (d8) was the most abundant labeled species (54%), but the sample also contained d7 (34%), and d6 (9%); as shown in Results, the deuterium content of 12R-HETE formed from this arachidonic acid was compared with that of 15-HETE prepared by reaction with soybean lipoxygenase (Sigma, type V). [10$_R$-$^3$H]- and [10$_s$-$^3$H]arachidonic acids were prepared from methyl 8-ketostearate, a gift from Dr Jin K. Cha (University of Alabama), through the following scheme: (i) reduction with NaB$^3$H$_4$, (ii) alkaline ester hydrolysis and preparation of the pentafluorobenzyl (PFB) ester, (iii) tosylation, (iv) resolution of the enantiomers by chiral phase HPLC (Chiralcel OD), (v) displacement of the tosylate with LiAlH$_4$, (vi) re-oxidation at C-1 with chromic acid, (vii) co-culture of the resulting [8$_R$-$^3$H] and [8$_s$-$^3$H]stearic acids mixed with [1-$^{14}$C]stearic acid with the fungus Saprolegnia parasitica, and (viii) resolution of the labeled arachidonic acids essentially as has been described previously (Maas et al. (1985) *J. Biol. Chem.* 260:4217–4228).

Incubation with Deuterated Arachidonic Acid—A sample of psoriatic scales (20–30 mg) was sonicated in 0.5 ml Medium 199 containing 40 mM Hepes, and incubated with 100 μM octadeuterated arachidonic acid for 1 hour at 37° C. The sample was extracted using the Bligh and Dyer method (Bligh et al. (1959) *Can. J. Biochem. Physiol.* 37:911–917) and the deuterated 12-HETE product was purified by RP-HPLC using a Beckman 5 μ ODS Ultrasphere column and a solvent of MeOH/H$_2$O/HAc (80/20/0.01, v/v/v). Care was taken to allow for the slightly more polar character (earlier elution) of the labeled product compared to unlabeled 12-HETE. The 12-HETE was further purified by SP-HPLC using an Alltech 5 µ Econosil column (25×0.46 cm) and a solvent of hexane:isopropanol:glacial acetic acid (100:2:0.1, v/v/v). It was then converted to the pentafluorobenzyl ester (PFB) derivative and purified again by SP-HPLC using a solvent of hexane/isopropanol (100:1, v/v). The resulting sample was analyzed on a Chiralcel OD HPLC column (25×0.46 cm) using a solvent of hexane:isopropanol (100:5, v/v) at a flow rate of 1.1 m/min with UV detection at 235 nm, as described in Brash et al. (1990) *Methods Enzymol.* 187:187–192.

GC-MS Analysis—HETE PFB esters were analyzed as the trimethylsilyl ether derivatives by GC-MS in the negative ion/chemical ionization mode using a Nermag R10-10C instrument, as described in Blair et al. (1990) *Methods Enzymol.* 187:13–23. Repetitive spectra were acquired by scanning over the mass range m/z 390–404, encompassing the major M-PFB ions at m/z 391 (unlabeled HETE) and m/z 399 (d8 analogue), essentially as described previously in Song et al. (1993) *J. Biol. Chem.* 268:6293–6298.

Experiments with Stereospecifically Labeled Arachidonic Acids—The specific activities of the two 10-$^3$H-labeled arachidonic acids were approximately 10,000–20,000 DPM $^3$H per µg. The pro-S [10-$^3$H]arachidonic acid was enriched in tritium by incubation with an 8R-lipoxygenase of Plexaura homomalla as described in principle previously in Hughes et al. (1991) *Biochim. Biophys. Acta* 1081:347–354. The stereospecifically-labeled arachidonic acids were admixed with [$^{14}$C]arachidonic acid which served as an internal standard for measurement of tritium retention. The final $^3$H/$^{14}$C ratios were in the range of 1.1–2.6 in different experiments.

Incubations were conducted in a volume of 0.2 ml 50 mM Tris pH 7.5, 100 mM NaCl, using (30,000 CPM $^3$H of stereospecifically-labeled arachidonic acids (mixed with [$^{14}$C]arachidonic acid) and (20 mg aliquots of psoriatic scales that were known to metabolize arachidonic acid to 12-HETE (patient #1) and 15-HETE +12-HETE (patient #2). The scales were sonicated briefly in the buffer and incubated for 90 min at 37° C. The samples were extracted with the Bligh and Dyer procedure (Bligh et al. (1959) *Can. J. Biochem. Physiol.* 37:911–917), including 1 µg triphenylphosphine to ensure reduction of any hydroperoxides. Products were purified by RP-HPLC (Beckman 5 µ ODS Ultrasphere, solvent MeOH/H$_2$O/HAc (80/20/0.01, v/v/v), by SP-HPLC of the methyl ester (Alltech 5 µ Econosil, hexane/isopropanol (100:1, v/v), and then by chiral phase HPLC (Chiralcel OD, hexane/isopropanol (100:2, v/v)). The 12R and 12S enantiomers were well resolved on the chiral column with retention times of 14 and 17.5 min respectively, and ≈1 min of baseline separation between the peaks. Fractions of 30 sec were collected across the eluting peaks, evaporated to dryness, mixed with scintillant and each counted for at least 60 min to define the $^3$H/$^{14}$C ratios of the baseline and the chromatographic peaks. Recovered 12R-HETE contained 150–500 CPM over background in the $^{14}$C channel.

Preparation of RNA, and cDNA synthesis—Samples of human scalp hair roots ((30 mainly anagen follicles) or psoriatic scales (100 mg) were placed in 1 ml TRI Reagent (Molecular Research Center, Inc.) and agitated in a bead beater for 20 seconds using autoclaved 200 micron glass beads. Keratinocyte RNA was prepared using 1.5 ml of TRI Reagent directly applied to a 10 cm plate of cultured cells and swirled to dissolve the RNA and protein. Total RNA was then extracted according to the manufacturer's instructions. mRNA was prepared from total RNA using the Oligotex mRNA Mini Kit (Qiagen). First strand cDNA was prepared using an oligo-dT-adapter primer. Preparation of hair follicle cDNA with adaptor primers (Marathon kit, Clontech) was performed as described in Brash et al. (1997) *Proc. Natl. Acad.:Sci. USA* 94:6148–6152.

PCR cloning—PCR reactions were primed with human hair follicle cDNA, keratinocyte cDNA, and in some experiments with cDNA prepared from psoriatic scales in a 50 µl reaction mixture of 10 mM Tris, pH 8.3, 50 mM KCl, 3 mM MgCl$_2$ with 0.2 mM of each dNTP and 0.25 µl (1.25 units) AmpliTaq DNA polymerase (Perkin Elmer) in a Perkin Elmer 480 thermocycler. After addition of cDNA (1 µl from a 50 µl cDNA synthesis) at 94° (hot start), the PCR was programmed as follows: 94° for 2 min, 1 cycle; 60° for 1 min, 72° for 1 min, 94° for 1 min, 30 cycles; 72° for 10 min, 1 cycle, and then the block temperature was held at 4° C. The primers were designed based on EST database entry AA649213 from human tonsillar cells. The upstream primer was 5'-C-AAC-TTC-CCA-GCG-TCC-ATG-CGT-AAT-CCA-3' (SEQ ID NO:3) versus the downstream primer 5'-TG-GTG-TTT-TGG-TCT-CTG-AGG-TTT-TTG-TGT-T-3' (SEQ ID NO:4), which corresponds to the 3' end of the open reading frame with the downstream primer in the UTR region. A band of 431 bp was produced.

The 5' RACE was accomplished using the Marathon cDNA Amplication Kit (Clontech) using 4 µg of total RNA from beard hair follicles, according to methods described in Brash et al. (1997) *Proc. Natl. Acad.:Sci. USA* 94:6148–6152. The gene-specific downstream primers were 5'-TGGTGTTTTGGTCTCTGAGGTTTTTGTGTT-3' (SEQ ID NO:5) and 5'-TTTTTGCTTGTTTGTTTTGTTTTGTTGAA-3' (SEQ ID N0:6).

A full length clone was obtained by PCR using primers purified by HPLC and using a proof-reading mixture of Taq/Pwo DNA polymerases (Expand High Fidelity, Boehringer-Mannheim) as described previously in Brash et al. (1997) *Proc. Natl. Acad.:Sci. USA* 94:6148–6152. The upstream primer encoded 5'-TTGGGCCTTCGTGTGGCCCTCCA-3' (SEQ ID NO:7), part of the 5' UTR about 30 bp upstream of the ATG translation start site. The downstream primer encoded the C-terminus of the protein: 5'-AGC-GCG-CTC-CTA-AAT-AGA-AAT-GCT-3' (SEQ ID NO:8). After a hot start at 94° C., the reaction conditions were 94°, 2 min, 1 cycle; 60° for 1 min, 72° for 2 min, 96° 15 sec, 30 cycles 72° 10 min, 1 cycle; hold at 4° C.

DNA sequencing—PCR products were subcloned into the pCR3.1 vector (Invitrogen) and sequenced by automated sequencing on an ABI Prism 377 Genetic analyzer and fluorescence-tagged dye terminator cycle sequencing (Perkin Elmer). Sequence similarities were calculated using the Jotun Hein algorithm of the Megalign program of Lasergene (DNASTAR Inc., Wis.).

Expression of cDNA, HPLC analysis of lipoxygenase metabolism—The PCR products corresponding to the open reading frame of the cDNA were ligated directly into bidirectional pCR3.1 (Invitrogen), clones with the correct orientation were selected by restriction enzyme digest, and these were then expressed by transient transfection in human Hela cells as described previously in Jisaka et al. (1997) *J. Biol. Chem.* 272:24410–24416. Initially twelve clones in pCR 3.1 were evaluated (ten expressed with equivalent activity), and subsequently an additional nine clones were expressed in pBluescript SK (four were active). Following incubation with substrate (50 or 100 µM [1-$^{14}$C]arachidonic acid or [1-$^{14}$C]linoleic acid) for 30 min at 37° C. in 50 mM Tris (pH 7.5) containing 150 mM NaCl, 0.1 mM CaCl$_2$, the products were extracted using the Bligh and Dyer procedure (Bligh et al. (1959) *Can. J. Biochem. Physiol.* 37:911–917) and treated with triphenylphosphine to reduce any hydroperoxides to HETEs. The extracts were analyzed by reversed-phase HPLC, normal phase HPLC and chiral phase HPLC, as described in Brash et al. (1990) *Methods Enzymol.* 187:187–192.

Northern Analysis—Three nylon membranes containing mRNA from human tissues (Clontech, Palo Alto, Calif.) were probed using a $^{32}$P-labeled EcoRI/NcoI 648 bp fragment of the new human lipoxygenase prepared from the plasmid and labeled by Rediprime random priming (Amersham). After hybridization in ExpressHyb solution (Clontech) at 68° C. for 1 hr, the membranes were washed finally in 0.1×SSC/0.1% SDS at 50° C. for 40 min and exposed to film. The same procedure was used for Northern analysis of human keratinocyte mRNA.

Detection of the mRNA in Human Psoriatic Scales—RNA was prepared using Tri Reagent (Molecular Research Center, Inc., Cincinnati, Ohio). Identical aliquots of the RNA samples were used in a cDNA synthesis reaction mixture with and without reverse transcriptase. PCR reactions were run with human keratinocyte cDNA as template, and also with psoriatic skin cDNA together with a parallel blank reaction without reverse transcriptase as a negative control.

Two pairs of primers were used, 5'-TGCCTGCTGCACTTTGGACC-3' (SEQ ID NO:9) with 5'-TGGTCTTCACATCCGGCAACGT-3' (SEQ ID NO:10) giving a 852 bp product, and 5'-CAACTTCCCAGCGTCCATGCGTAATCCA-3' (SEQ ID NO:11) with 5'-TGGTGTTTTGGTCTCTGAGGTTTTTGTGTT-3' (SEQ ID NO:12) giving a 431 bp product. Both reactions were run using an annealing temperature of 60° in the PCR.

Results

Investigation of a Potential Isomerization of 12S- to 12R-HETE—One potential pathway to 12R-HETE is via synthesis of 12S-H(P)ETE, followed by oxidation to the 12-keto analogue and reduction back to 12R-HETE. To address the possible existence of this pathway in psoriatic scales, the retention of deuterium in the biosynthesis of 12R-HETE from octadeuterated arachidonic acid was measured. This substrate contains a deuterium label at C-12 which would be lost upon formation of a keto intermediate.

Figure 1B:
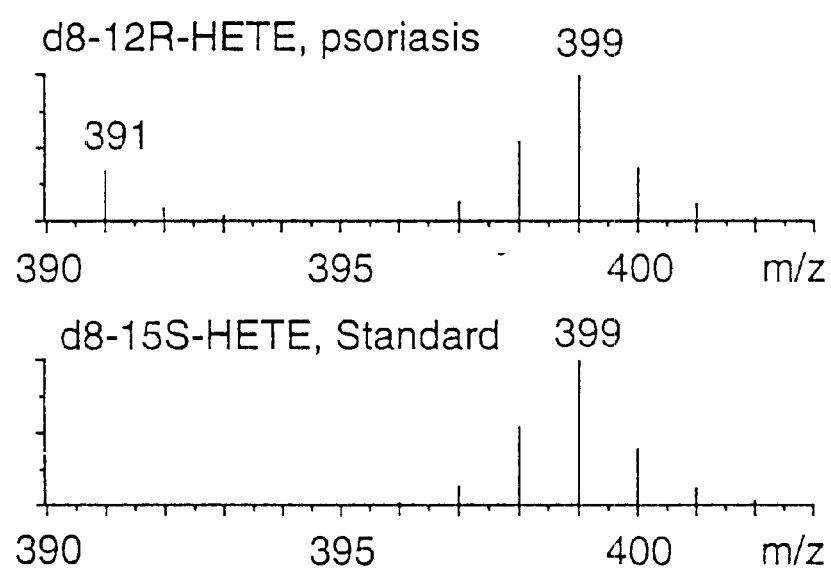
FIG. 1B depicts partial mass spectra of the 12R-HETE from panel A (top), and 15S-HETE prepared from the same batch of deuterated arachidonic acid using the soybean lipoxygenase (as described below). The samples were analyzed by negative ion/chemical ionization GC-MS as the PFB ester trimethylsilyl ether derivatives by repetitive scanning in the range m/z 390–404. The partial mass spectra are the average of all scans collected during elution of the peaks from the GC. Unlabeled 12R-HETE is also detected in the psoriatic sample at m/z 391.

Following incubation of octadeuterated arachidonic acid with psoriatic scales, the 12-HETE was isolated, the 12R and 12S enantiomers were resolved by chiral phase HPLC (FIG. 1A), and the deuterium content of the 12R-HETE was measured by mass spectrometry (FIG. 1B). For direct comparison with a reaction involving no loss of deuterium, the 12R-HETE spectrum in FIG. 1B is compared to that of labeled 15-HETE prepared from the same batch of deuterated arachidonic acid using the soybean lipoxygenase. The deuterium content of the 12R-HETE and the 15-HETE are indistinguishable (and identical to that of d$_8$-15-HETE formed in the psoriatic scales, not shown), indicating no loss of label in the formation of 12R-HETE and thus eliminating keto-hydroxy rearrangements as a route to 12R-HETE in psoriatic skin.

Stereospecificity of Hydrogen Abstraction in 12R-HETE Biosynthesis—Conversion of arachidonic acid to 12-HETE requires removal of one of the two methylene hydrogens on the 10-carbon. A cytochrome P450 and 12R-lipoxygenase would show different stereoselectivity in this hydrogen abstraction. Cytochrome P450s tend to exhibit a suprafacial relationship between hydrogen abstraction and oxygen insertion, i.e. the two occur on the same face of the substrate (White et al. (1986) *J. Am. Chem. Soc.* 108:6024–6031; Oliw et al. (1993) *Arch. Biochem. Biophys.* 300:434–439). By contrast, with lipoxygenases the two occur on opposite faces (an antarafacial relationship) (e.g., Hawkins et al. (1987) *J. Biol. Chem.* 262:7629–7634; Hamberg et al. (1967) *J. Biol. Chem.* 242:5329–5335; Egmond et al. (1972) *Biochem. Biophys. Res. Commun.* 48:1055–1060; Hamberg et al. (1980) *Biochem. Biophys. Res. Commun.* 95:1090–1097; Maas et al. (1982) *J. Biol. Chem.* 257:13525–13519).

This feature of 12R-HETE synthesis was examined by conducting incubations of psoriatic scales with arachidonic acids containing a pro-R or pro-S tritium label on the 10-carbon (with [$^{14}$C]arachidonic acid included to standardize the measurements of tritium retention). The 12-HETE product from each incubation was purified by HPLC and the 12R and 12S enantiomers were resolved by chiral phase HPLC. The 12R enantiomer accounted for 80–90% of the 12-HETE product from psoriatic skin. The tritium retention was determined from the $^{3}$H/$^{14}$C ratio by liquid scintillation counting (Table 2).

Figure 5:
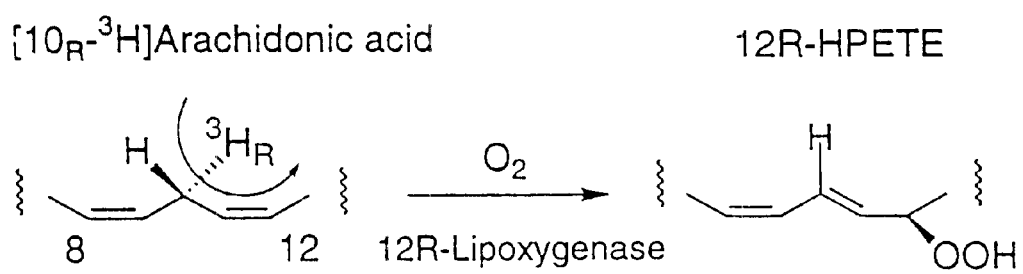
FIG. 5 is a reaction scheme illustrating the reaction mechanism of the 12R-lipoxygenase of the present invention.

Arachidonic acid with a pro-R 10-$^{3}$H label gave rise to 12R-HETE that had lost virtually all the tritium (Table 2, first column). This is exactly as predicted for catalysis by a 12R-lipoxygenase (Scheme in FIG. 5), and indeed it matches the result obtained with the 12R-lipoxygenase to be described below (Table 2). Using the arachidonic acid substrate with the pro-S $^{3}$H label at C-10, the 12R-HETE product retained about 85% of the tritium. This is compatible with results obtained in other lipoxygenase-catalyzed reactions in which a secondary isotope effect slightly slows the rate of reaction of the $^{3}$H-labeled molecules resulting in less than 100% $^{3}$H retention in the product (Maas et al. (1982) *J. Biol. Chem.* 257:13525–13519; Brash et al. (1986) *Biochim. Biophys. Acta* 875:256–261). These results indicate no significant P450 involvement in 12R-HETE synthesis under the conditions of these experiments and directly indicate a 12R-lipoxygenase pathway.

Molecular Cloning of a Novel Human Lipoxygenase—The initial clone of a novel human lipoxygenase was obtained using hair follicle and keratinocyte cDNAs as template and primers based on sequence from a human EST (GenBank, AA649213). The published sequence comprised approximately 500 bp encoding the 3' end of the open reading frame and 150 bp of 3' UTR. The sequence clearly encoded a previously undescribed lipoxygenase. The 5' end of the lipoxygenase transcript was obtained by 5' RACE using human hair follicle cDNA as template. The cDNA encoding the complete open reading frame (the open reading frame is from nucleotides 260–2362 inclusive) was then prepared by PCR and subcloned into the pCR 3.1 vector. Two of the active clones described below were sequenced (FIGS. 2A–2E).

The novel lipoxygenase cDNA has approximately 50% similarity in sequence to the second type of human 15S-lipoxygenase (Brash et al. (1997) *Proc. Natl. Acad Sci. USA* 94:6148–6152), and 40% to the human 5S-lipoxygenase. It is more distantly related to the 12S- and reticulocyte-type of 15S-lipoxygenase (38% and 35% similarity, respectively). The new human sequence is closely related to a recently reported mouse lipoxygenase cDNA ((86% identity) (Krieg et al. (1998) *Biochim. Biophys. Acta* 1391:7–12).

Figure 3A:
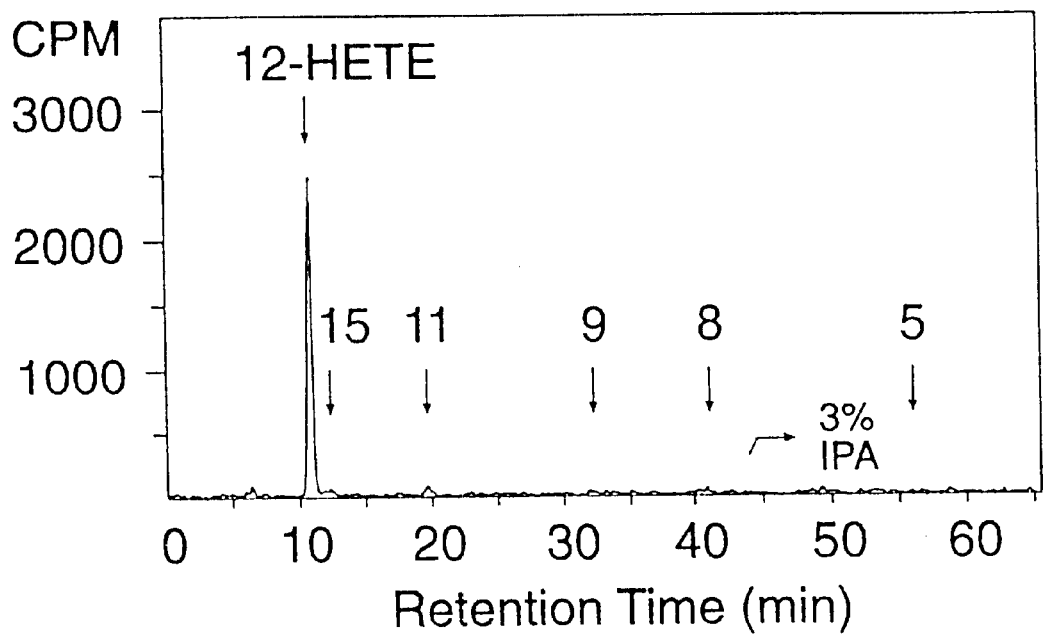
FIG. 3A depicts product analysis by normal-phase HPLC using an Alltech 5µ Econosil silica column (25×0.46 cm), a solvent system of hexane:isopropanol:glacial acetic acid (100:1:0.1, by volume, changed to the proportions 100:3:0.1 at 45 min), and a flow rate of 1.1 ml/min with on-line detection of radiolabeled products using a Packard Flo-One Radiomatic detector. Retention times of unlabeled HETE standards (co-injected with the $^{14}C$ sample) are indicated on the chromatogram.
Figure 3B:
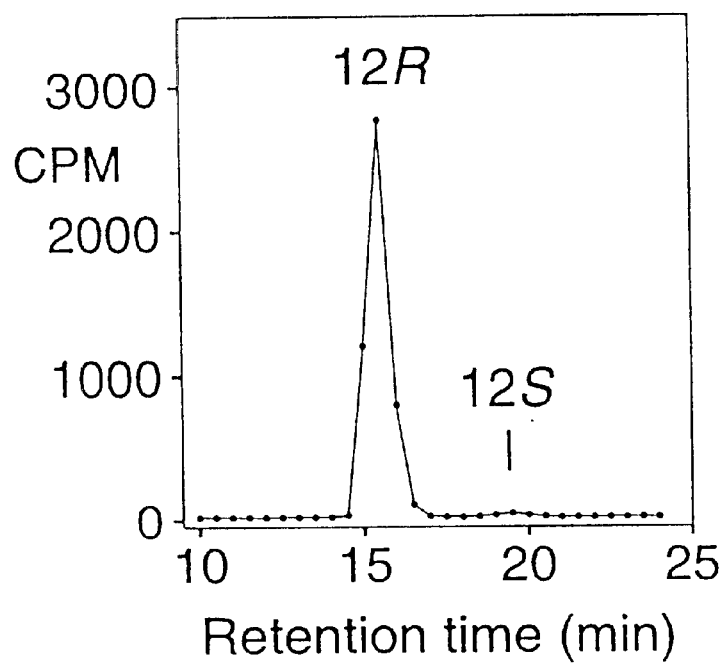
FIG. 3B depicts chiral analysis of the methyl ester derivative of the 12-HETE using a Chiralcel OD column with a solvent of hexane:isopropanol (100:2, v/v) and a flow rate of 1.1 ml/min.

Expression of the cDNA - The cDNA was transfected into vaccinia infected Hela cells and after 20 hours the cell sonicates were evaluated for lipoxygenase activity by incubation with [$^{14}$C]arachidonic acid and HPLC analysis (Experimental Procedures). Reversed-phase HPLC analysis with on-line recording of UV spectra and radioactive monitoring showed a single major product with a conjugated diene UV spectrum and which co-chromatographed with 12-HETE and 8-HETE. The HETEs were collected as a group from RP-HPLC and further analyzed by normal-phase HPLC as shown in FIG. 3A. The single main product was identified as 12-HETE on the basis of its co-chromatography with the authentic standard and its identical UV spectrum ($\lambda_{max}$ 237 nm, indicative of the 8cis-10trans conjugation). Minor amounts of 15-HETE and 11-HETE were present. The 12-HETE product was 98% of the 12R configuration (FIG. 3B). The primary 12-lipoxygenase product, 12R-HPETE, was detectable in incubations of baculovirus/insect cell-expressed enzyme, confirming that the new enzyme is a 12R-lipoxygenase. Linoleic acid was a relatively poor substrate for the 12R-lipoxygenase compared to arachidonic acid.

Figures 4A, 4B:
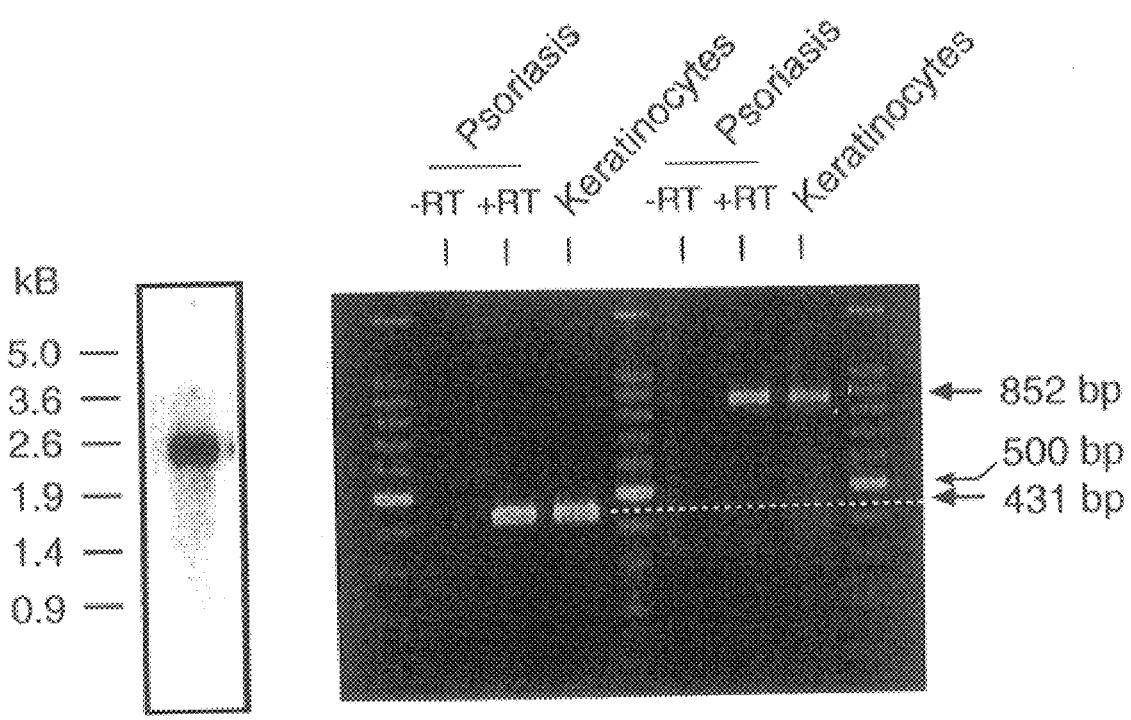
FIG. 4A is an autoradiograph of northern blot analysis of human keratinocytes.
FIG. 4B is a photograph of agarose gel chromatography depicting detection of the transcript of the 12R-lipoxygenase of the present invention in human keratinocytes and psoriatic scales by RT-PCR. Paired RNA samples prepared from psoriatic scales were run in parallel reactions with or without reverse transcriptase (+RT, −RT). PCR reactions were then run using two primer sets (see Experimental Procedures of Example 1 hereinbelow) including human keratinocyte cDNA as a positive control. Three lanes contain DNA size markers (100 bp ladder), and the bright band in the middle is 500 bp.

Tissue Expression of the 12R-lipoxygenase—Northern analysis of human keratinocytes using a 12R-lipoxygenase-specific probe gave a single band of 2.5 kB (FIG. 4A), compatible with the predicted size of the mRNA comprising 260 bp of 5' UTR, 2103 bp open reading frame, and 150 bp 3' UTR. No distinct hybridization was observed by Northern analysis of three human multiple tissue Northern blots comprising the following tissues from normal subjects: spleen, thymus, prostate, testis, ovary, small intestine, colon, peripheral blood leukocytes, heart, brain, placenta, lung, liver, skeletal muscle, kidney, pancreas, stomach, thyroid, spinal cord, lymph node, trachea, adrenal gland, and bone marrow. The mRNA could be detected by RT-PCR in cDNA prepared from human hair follicles, human foreskin keratinocytes, and (with uncertain prospects for recovery of mRNA) in one of two samples prepared from the scaly discarded skin of subjects with psoriasis (FIG. 4B).

Discussion of Results

The presence of 12R-HETE in psoriatic lesions is a recognized feature of the disease, yet until the isolation of the 12R-lipoxygenase described above, its enzymatic origin has remained elusive. All the known mammalian lipoxygenases form S configuration hydroperoxides (Funk, C. D. (1993) *Prog. Nuc. Acid Res. Mol. Biol.* 45:67–98); this biased against a potential 12R-lipoxygenase pathway. Cytochromes P450 can convert arachidonic acid to a mixture of oxygenated derivatives that include 12R-HETE (Capdevila et al. (1986) *Biochem. Biophys. Res. Commun.* 141:1007–1011; Oliw, E. H. (1993) *Biochim. Biophys. Acta* 1166:258–263; Bylund et al. (1998) *J. Pharmacol. Exp. Ther.* 284:51–60), but the distinctive aspect of 12R-HETE production in human skin is its appearance together with very few other products (mainly 12S- and 15S-HETEs). Direct biochemical characterization of the enzyme proved difficult using small amounts of human tissue. For example, NADPH-dependence is not definitively diagnostic for a P450-type of monooxygenase; lipoxygenases in tissue extracts are sensitive to the redox environment and can show changes in catalytic activity in the presence of reducing cofactors (Cochran et al. (189) *Biochem. Biophys. Res. Commun.* 161:1327–1332; Riendeau et al. (1989) *Biochem. J.* 263:65–572; Shornick et al. (1993) *J. Biol. Chem.* 268:371–376). For all these reasons, the enzyme responsible for 12R-HETE production was previously uncharacterized.

In the initial series of experiments described herein, a mechanistic approach was used to address the enzymatic origin of 12R-HETE in psoriatic scales. The first potential route that was considered was a rearrangement from 12S-H(P)ETE through a 12-keto intermediate. Interconversion of 12R- and 12S-HETEs via the ketone is precedented in rat liver, skin and leukocyte microsomes, although in these cases the final reduction favors formation of 12S-HETE (Falgueyret et al. (1988) *Biochem. Biophys. Res. Commun.* 156:1083–1089; Falgueyret et al. (1990) *FEBS Lett.* 262:197–200). Nonetheless, in principle the formation of 12R-HETE could occur in skin with the known 12S-lipoxygenase providing the initial substrate. This pathway to 12R-HETE was excluded based on the retention of a C-12 deuterium label during the biosynthesis (FIG. 1B).

The other two possibilities, a cytochrome P450 type of monooxygenase or a 12R-lipoxygenase, each involve direct oxygenation into the 12R configuration. In principle, the two pathways can be distinguished by the initial formation of a 12R-hydroperoxide in the lipoxygenase-catalyzed reaction. This intermediate, however, is readily reduced in a crude tissue extract and its detection is particularly problematic when low levels of the product are formed. An alternative method which relies on analysis of 12R-HETE, the common end product of the two potential pathways, was adopted. Applicants measured the retention of tritium in the 12R-HETE after incubation of psoriatic scales with arachidonic acid substrates containing a prochiral tritium label on the 10-carbon. Invariably, lipoxygenases catalyze a stereoselective oxygenation with removal of the prochiral hydrogen from the opposite face of the substrate (Hamberg et al. (1967) *J. Biol. Chem.* 242:5329–5335; Egmond et al. (1972) *Biochem. Biophys. Res. Commun.* 48:1055–1060; Hamberg et al. (1980) *Biochem. Biophys. Res. Commun.* 95:1090–1097; Maas et al. (1982) *J. Biol. Chem.* 257:13525–13519). This is not observed in P450-catalyzed reactions. With P450s, the hydrogen removal and oxygenation exhibit a suprafacial relationship, often mixed with an element of stereorandom hydrogen abstraction (White et al. (1986) *J. Am. Chem. Soc.* 108:6024–6031; Oliw et al. (1993) *Arch. Biochem.Biophys.* 300:434–439).

The above described studies in psoriatic scales provided an unequivocal result. The 12R-HETE formed from [10$_R$-$^3$H]arachidonic acid contained almost no tritium (Table 2). This indicates there is an antarafacial relationship between hydrogen abstraction and 12R oxygenation, a result compatible only with a 12R-lipoxygenase catalyzed transformation (Scheme in FIG. 5). The human 12R-lipoxygenase that has been cloned and expressed displays the same characteristics (Table 2).

With the emerging evidence from the mechanism-based experiments for the existence of a human 12R-lipoxygenase, a cloning strategy similar to that had led to discovery of the second type of human 15S-lipoxygenase, as described in Brash et al. (1997) *Proc. Natl. Acad.Sci. USA* 94:6148–6152, was initiated. Applicants also utilized primers from a recently released EST sequence (GenBank, AA649213) to begin characterization of the cDNA of the human 12R-lipoxygenase. The EST sequence was obtained from human tonsillar cells enriched for germinal center B cells.

The 12R-lipoxygenase cDNA is somewhat unusual in having 260 bp of 5' UTR and a short sequence (150 bp) of 3' UTR. The open reading frame encodes a protein with all the typical characteristics and conserved amino acids of animal lipoxygenases. It also encodes approximately 5 kD of extra sequence, accounted for by an insert of 31 amino acids. A similar 31 amino acid sequence, but wherein 6 of 31 amino acids were different, was observed in the recently reported mouse lipoxygenase cDNA referenced above. (Krieg et al. (1998) *Biochim. Biophys. Acta* 1391:7–12). By reference to the crystal structure of the rabbit reticulocyte 15S-lipoxygenase (Gillmor et al.). (1997) *Nature Struct. Biol.* 4:1003–1009), the extra sequence in the 12R-lipoxygenase is located after the first alpha-helix of the main C-terminal domain. In this position it can be accomodated on the outside of the protein without disruption of the overall tertiary structure. The 31 amino acid insert includes seven prolines and five arginines. While there is not a perfect consensus sequence of, for example, a proline-rich SH3-binding domain (Lepley et al. (1994) *J. Biol. Chem.* 269:24163–24168), this extra sequence of the 12R-lipoxygenase could well be involved in regulatory protein—protein interactions.

Applicants were able to establish the 12R-lipoxygenase activity of the enzyme expressed in Hela cells (and additionally in baculovirus/insect cells, not shown), yet the expressed protein has low catalytic activity. It expressed with 10-fold lower activity than the reticulocyte-type of 15-lipoxygenase that we used as a positive control in each experiment. This is similar to observations with the murine 8S-lipoxygenase and epidermal-type of 12S-lipoxygenase (Jisaka et al. (1997) *J. Biol. Chem.* 272:24410–24416; Funk et al. (1996) *J. Biol. Chem.* 271 :23338–23344), both of which also express with weak catalytic activity in vitro. In psoriatic scales, the production of 12R-HETE and 15S-HETE are often of the same order of magnitude (Baer et al. (1991) *J. Lipid Research* 32:341–347). To account for this, either there is a major difference in the respective levels of the 12R- and 15S-lipoxygenases, or the activity of the 12R-lipoxygenase is increased under natural circumstances by protein modification or interactions with other component(s) of the tissue.

It was established from the previously described cloning of 8R-lipoxygenases from coral that the R- and S-lipoxygenases are members of the same gene family (Brash et al. (1996) *J. Biol. Chem.* 271:20549–20557; Koljak et al. (1997) *Science* 277:1994–1996). Characterization of the 12R-lipoxygenase now extends the known occurrence of R-lipoxygenases beyond the realm of marine and freshwater invertebrates. The mRNA for the human 12R-lipoxygenase has been detected in hair roots, in primary cultures of foreskin keratinocytes, and by PCR, in a sample of psoriatic scales. With the tools made available through molecular cloning the involvement of this enzyme in the cell proliferation and inflammation of psoriasis can be approached according to the methods described hereinabove.

TABLE 2

Stereospecificity of C-10 Hydrogen Abstraction in 12R-HETE Biosynthesis

| Sample | ProR[10-$^3$H]20.4ω6 substrate % Tritium Retention in 12R-HETE | ProS[10-$^3$H]20.4ω6 subsbate |
|---|---|---|
| Psoriatic scales, patient #1 | 2 | 85 |
| Psoriatic scales, patient #2 | 1 | 89 |
| 12R-Lipoxygenase[a] | 1 | 83 |

[a]The cDNA (FIGa. 2A–2E) expressed in Hela cells.

REFERENCES

Adelman et al. (1983) DNA 2:183.
Ausubel et al. (1992) *Current Protocols in Molecular Biology*, (J. Wylie & Sons, N.Y.)
Baer et al. (1991) *J. Lipid Research* 32:341–347.
Baer et al. (1993) *J. Lipid Research* 34:1505–1514.
Baer et al. (1995) *J. Invest. Dermatol.* 104:251–255.
Blair et al. (1990) *Methods Enzymol.* 187:13–23.
Bligh et al. (1959) *Can. J. Biochem. Physiol.* 37:911–917.
Brash et al. (1986) *Biochim. Biophys. Acta* 875:256–261.
Brash et al. (1990) *Methods Enzymol.* 187:187–192.
Brash et al. (1996) *J. Biol. Chem.* 271:20949–20957.
Brash et al. (1997) *Proc. Natl. Acad:Sci. USA* 94:6148–6152.
Burr et al. (1929) *J. Biol. Chem.* 82:345–367.
Burrall et al. (1988) *J. Invest. Dermatol.* 4:294–297.
Bylund et al. (1998) *J. Pharmacol. Exp. Ther.* 284:51–60.
Capdevila et al. (1986) *Biochem. Biophys. Res. Commun.* 141:1007–1011.
Cochran et al. (189) *Biochem. Biophys. Res. Commun.* 161:1327–1332.
Crea et al., (1978) *Proc. Natl. Acad. Sci. U.S.A,* 75:5765.
Dixon et al. (1988) *Proc. Natl. Acad. Sci. USA* 85:416–420.
Egmond et al. (1972) *Biochem. Biophys. Res. Commun.* 48:1055–1060.
Eichenlaub et al. R. *J. Bacteriol* 138:559–566, 1979.
Falgueyret et al. (1988) *Biochem. Biophys. Res. Commun.* 156:1083–1089.
Falgueyret et al. (1990) *FEBS Lett.* 262:197–200.
Funk et al. (1990) *Proc. Natl. Acad. Sci. USA* 87:5638–5642.
Funk et al. (1993) *Prog. Nuc. Acid Res. Mol. Biol.* 45:67–98.
Funk et al. (1996) *J. Biol. Chem.* 271:23338–23344.
Gillmor et al. (1997) *Nature Struct. Biol.* 4:1003–1009.
Green et al. (1989) *J. Invest. Dermatol.* 93:486–491.
Hamberg et al. (1980) *Biochem. Biophys. Res. Commun.* 95:1090–1097.
Hamberg et al. (1967) *J. Biol. Chem.* 242:5329–5335.
Hammarström et al. (1975) *Proc. Natl. Acad. Sci. USA* 72:5130–5134.
Hawkins et al. (1987) *J. Biol. Chem.* 262:7629–7634.
Hawkins et al. (1989) *FEBS Lett.* 247:9–12.
Henneicke-von Zepelin et al. (1991) *J. Invest. Dermatol.* 97:291–297.
Holtzman et al. (1989) *J. Clin. Invest.* 84:1446–1453.
Hopp, U.S. Pat. No. 4,554,101.
Howell et al. (1988) *Antibodies A Laboratory Manual,* (Cold Spring Harbor Laboratory).
Hughes et al. (1991) *Biochim. Biophys. Acta* 1081:347–354.
Hussain et al. (1994) *Am. J. Physiol.* 266:C243–C253.
Izumi et al. (1990) *Proc. Natl. Acad. Sci. USA* 87:7477–7481.
Jisaka et al. (1997) *J. Biol. Chem.* 272:24410–24416.
Johnson et al., PCT Publication WO 93/25521, published Dec. 23, 1993
Koljak et al. (1997) *Science* 277:1994–1996.
Krieg et al. (1998) *Biochim. Biophys. Acta* 1391:7–12.
Kyte et al. (1982) *J. Mol. Biol.* 157: 105.
Lepley et al. (1994) *J. Biol. Chem.* 269:24163–24168.
Maas et al. (1982) *J. Biol. Chem.* 257:13525–13519.
Maas et al. (1985) *J. Biol Chem.* 260:4217–4228.
Marnett et al., U.S. Pat. No. 5,234,933.
Matsumoto et al. (1988) *Proc. Natl. Acad. Sci. USA* 85:26–30.
Messing et al. (1981) *Third Cleveland Symposium on Macromolecules and Recombinant NA*, Editor A. Walton, (Elsevier, Amsterdam).
Nugteren et al. (1985) *Biochim. Biophys. Acta* 834:429–436.
Nugteren et al. (1987) *Biochim. Biophys. Acta* 921:135–141.
Oliw et al. (1993) *Arch. Biochem. Biophys.* 300:434–439.

Oliw et al. (1993) *Biochim. Biophys. Acta* 1166:258–263.
Riendeau et al. (1989) *Biochem. J.* 263:65–572.
Sambrook et al. (1989) *Molecular Cloning: A Laboratory Manual* (Cold Spring Harbor Laboratory Press, Cold Spring Harbor, N.Y.).
Seipp et al., U.S. Pat. No. 5,326,902.
Shornick et al. (1993) *J. Biol. Chem.* 268:371–376.
Sigal et al. (1988) *Biochem. Biophys. Res. Comm.* 157: 457–464.
Song et al. (1993) *J. Biol. Chem.* 268:6293–6298.
Taber et al. (1982) *Methods Enzymol.* 86:366–369.
Takahashi et al. (1993) *J. Biol. Chem.* 268:16443–16448.
U.S. Pat. No. 2,868,691
U.S. Pat. No. 3,095,355
U.S. Pat. No. 4,196,265
U.S. Pat. No. 4,683,202
U.S. Pat. No. 4,736,866
U.S. Pat. No. 5,162,215
U.S. Pat. No. 5,489,742
U.S. Pat. No. 5,550,316
U.S. Pat. No. 5,573,933
U.S. Pat. No. 5,614,396
U.S. Pat. No. 5,625,125
U.S. Pat. No. 5,627,158
U.S. Pat. No. 5,645,999
U.S. Pat. No. 5,648,061
U.S. Pat. No. 5,734,033
U.S. Pat. No. 5,741,957
Wetmur & Davidson (1968) *J. Mol. Biol.* 31:349–370.
White et al. (1986) *J. Am. Chem. Soc.* 108:6024–6031.
Woollard, P. M. (1986) *Biochem. Biophys. Res. Commun.* 136:169–175.
Yoshimoto et al. (1990) *Biochem. Biophys. Res. Comm.* 172:1230–1235.
Yu et al. (1995) *J. Biol. Chem.* 270:23975–23983.
Zhao et al. (1995) *J. Lipid Res.* 36:24444–2449.
Ziboh et al. (1996) *Lipids* 31: S249–S253.

What is claimed is:

1. An isolated and purified biologically active human 12R-LO polypeptide that metabolizes arachidonic acid to 12R-hyrdroxyeicosatetraenoic acid, wherein the 12R-LO polypeptide comprises:
    (a) the amino acid sequence of SEQ ID NO:2; or
    (b) the amino acid sequence of SEQ ID NO:2, wherein one or more amino acids are substituted with a biologically equivalent amino acid.

2. An isolated and purified biologically active human 12R-LO polypeptide that metabolizes arachidonic acid to 12R-hydroxyeicosatetraenoic acid, wherein the 12R-LO polypeptide comprises the amino acid sequence of SEQ ID NO:2.

3. The polypeptide of claim 1, modified to be in detectably labeled form.

4. A process of producing an antibody immunoreactive with a lipoxygenase polypeptide, the process comprising steps of:
    (a) transfecting a recombinant host cell with a nucleic acid segment encoding a 12R-LO polypeptide, wherein the 12R-LO polypeptide comprises:
        (i) the amino acid sequence of SEQ ID NO:2; or
        (ii) the amino acid sequence of SEQ ID NO:2, wherein one or more amino acids are substituted with a biologically equivalent amino acid;
    (b) culturing the host cell under conditions sufficient for expression of the polypeptide;
    (c) recovering the polypeptide; and
    (d) preparing the antibody to the polypeptide.

5. The process of claim 4, wherein the polypeptide comprises SEQ ID NO:2.

6. The process of claim 4, wherein the nucleic acid segment comprises SEQ ID NO:1.

7. A diagnostic assay kit for detecting the presence, in a biological sample, of an antibody immunoreactive with a lipoxygenase polypeptide, the kit comprising a first container containing a lipoxygenase polypeptide of claim 1 that immunoreacts with the antibody, with the polypeptide present in an amount sufficient to perform at least one assay.

8. A method of screening candidate substances for their ability to modulate arachidonic acid metabolism, the method comprising the steps of:
    (a) establishing replicate test and control samples that comprise arachidonic acid and a human 12R-LO polypeptide that metabolizes arachidonic acid to 12R-hydroxyeicosatetraenoic acid, wherein the human 12R-LO polypeptide comprises:
        (i) the amino acid sequence of SEQ ID NO:2 or
        (ii) the amino acid sequence of SEQ ID NO:2, wherein one or more amino acids are substituted with a biologically equivalent amino acid
    (b) administering a candidate substance to the test sample but not the control sample;
    (c) measuring 12R-hydroxyeicosatetraenoic acid levels in the test and the control samples; and
    (d) determining that the candidate substance modulates arachidonic acid metabolism if the 12R-hydroxyeicosatetraenoic acid level measured for the test sample is greater or less than the 12R-hydroxyeicosatetraenoic acid level measured for the control sample.

9. The method of claim 8, wherein the replicate test and control samples further comprise a cell that expresses the human 12R-LO polypeptide that metabolizes arachidonic acid to 12R-hydroxyeicosatetraenoic acid.

10. A recombinant cell line suitable for use in the method of claim 9.

11. The polypeptide of claim 1, wherein the polypeptide is encoded by a nucleic acid molecule comprising SEQ ID NO:1.

12. An isolated and purified biologically active 12R-LO polypeptide that metabolizes arachidonic acid to 12R-hydroxyeicosatetraenoic acid, further characterized as a polypeptide encoded by an isolated nucleic acid segment selected from the group consisting of:
    (a) an isolated nucleic acid segment which hybridizes to the nucleic acid sequence given herein as SEQ ID NO:1 under wash stringency conditions represented by a wash solution having less than about 200 mM salt concentration and a wash temperature of greater than about 45° C., and which encodes a 12R-LO polypeptide; and
    (b) an isolated nucleic acid segment differing by at least one functionally equivalent codon from the isolated nucleic acid molecule of (a) above in nucleic acid sequence due to the degeneracy of the genetic code, and which encodes a human 12R-LO polypeptide encoded by the isolated nucleic acid of (a) above.

13. The process of claim 4, wherein the nucleic acid segment comprises SEQ ID NO:1.

14. The process of claim 4, wherein the nucleic acid segment is selected from the group consisting of:
    (a) an isolated nucleic acid segment which hybridizes to the nucleic acid sequence given herein as SEQ ID NO:1 under wash stringency conditions represented by a wash solution having less than about 200 mM salt concentration and a wash temperature of greater than about 45° C., and which encodes a 12R-LO polypeptide; and
    (b) an isolated nucleic acid segment differing by at least one functionally equivalent codon from the isolated nucleic acid molecule of (a) above in nucleic acid sequence due to the degeneracy of the genetic code, and which encodes a 12R-LO polypeptide encoded by the isolated nucleic acid of (a) above.

15. A diagnostic assay kit for detecting the presence in a biological sample, of an antibody immunoreactive with a 12R-LO polypeptide, the kit comprising a first containing a 12R-LO polypeptide of claim 12 that immunoreacts with the antibody, with the polypeptide present in an amount sufficient to perform at least one assay.

16. A process of producing an antibody immunoreactive with a lipoxygenase polypeptide, the process comprising steps of:
    (a) transfecting a recombinant host cell with a nucleic acid segment encoding a 12R-LO polypeptide, wherein the nucleic acid segment comprises:
        (i) an isolated nucleic acid segment which hybridizes to the nucleic acid sequence given herein as SEQ ID NO:1 under wash stringency conditions represented by a wash solution having less than about 200 mM salt concentration and a wash temperature of greater than about 45° C., and which encodes a 12R-LO polypeptide; and
        (ii) an isolated nucleic acid segment differing by at least one functionally equivalent codon from the isolated nucleic acid molecule of (i) above in nucleic acid sequence due to the degeneracy of the genetic code, and which encodes a 12R-LO polypeptide encoded by the isolated nucleic acid of (i) above;

(b) culturing the host cell under conditions sufficient for expression of the polypeptide;

(c) recovering the polypeptide; and (d) preparing the antibody to the polypeptide.

17. A method of screening candidate substances for their ability to modulate arachidonic acid metabolism, the method comprising the steps of:

(a) establishing replicate test and control samples that comprise arachidonic acid and the 12R-LO polypeptide of claim 12;

(b) administering a candidate substance to the test sample but not the control sample;

(c) measuring 12R-hydroxyeicosatetraenoic acid levels in the test and the control samples; and (d) determining that the candidate substance modulates arachidonic acid metabolism if the 12R-hydroxyeicosatetraenoic acid level measured for the test sample is greater or less than the 12R-hydroxyeicosatetraenoic acid level measured for the control sample.

18. The method of claim 17, wherein the replicate test and control samples further comprise a cell that expresses the 12R-LO polypeptide.

* * * * *

```
                          SEQUENCE LISTING

<160> NUMBER OF SEQ ID NOS: 12

<210> SEQ ID NO 1
<211> LENGTH: 2469
<212> TYPE: DNA
<213> ORGANISM: Homo sapiens
<220> FEATURE:
<221> NAME/KEY: CDS
<222> LOCATION: (260)..(2362)

<400> SEQUENCE: 1
cccagacacc tgctcactca ccaccagctg ggctccgctg ggcctgcccg gcacccaccc        60
cggccaccaa gggcagcagc ttttccagaa tttggctggc aggcctagtc accccacctc       120
gccacctcac cactgcacct cggaggccag ccctgtccac tccactctgt gcctggcttc       180
tcttgcctgc cttgggcctt cgtgtggccc tccacggtgt ctgggactga gtgcccctct       240
tgcctcctga agagcagcc atg gcc acc tac aaa gtc agg gtg gcc aca ggc       292
                      Met Ala Thr Tyr Lys Val Arg Val Ala Thr Gly
                        1               5                  10 acc gac ctc ttg tcg gga aca cgg gac tcc atc tca ctg acc att gtg       340
Thr Asp Leu Leu Ser Gly Thr Arg Asp Ser Ile Ser Leu Thr Ile Val
            15                  20                  25 ggg aca caa gga gag agc cat aag cag ctg ctg aac cac ttt ggg aga       388
Gly Thr Gln Gly Glu Ser His Lys Gln Leu Leu Asn His Phe Gly Arg
        30                  35                  40 gac ttt gca act ggg gcg gtg ggc cag tac acc gtg cag tgc cct cag       436
Asp Phe Ala Thr Gly Ala Val Gly Gln Tyr Thr Val Gln Cys Pro Gln
    45                  50                  55 gac ctg ggt gag ctc atc atc atc cgc ctg cac aaa gag cgg tac gcc       484
Asp Leu Gly Glu Leu Ile Ile Ile Arg Leu His Lys Glu Arg Tyr Ala
60                  65                  70                  75 ttc ttc ccc aag gac cct tgg tac tgc aac tat gtg cag atc tgt gcc       532
Phe Phe Pro Lys Asp Pro Trp Tyr Cys Asn Tyr Val Gln Ile Cys Ala
                80                  85                  90 ccc aac ggc cgt atc tac cac ttc ccc gcc tac cag tgg atg gat ggc       580
Pro Asn Gly Arg Ile Tyr His Phe Pro Ala Tyr Gln Trp Met Asp Gly
            95                 100                 105 tac gag acc ctg gca ctc cgg gag gcc aca gga aag aca aca gca gat       628
Tyr Glu Thr Leu Ala Leu Arg Glu Ala Thr Gly Lys Thr Thr Ala Asp
        110                 115                 120
```

```
gac tcg ctc ccc gtc ctc ctg gag cac aga aaa gag gag atc aga gcc      676
Asp Ser Leu Pro Val Leu Leu Glu His Arg Lys Glu Glu Ile Arg Ala
    125                 130                 135 aag cag gac ttc tac cac tgg cga gtc ttt ctt cct ggc ctg ccc agc      724
Lys Gln Asp Phe Tyr His Trp Arg Val Phe Leu Pro Gly Leu Pro Ser
140                 145                 150                 155 tat gtg cac att ccc agt tac cgc cct ccg gtg cgg agg cat cgc aac      772
Tyr Val His Ile Pro Ser Tyr Arg Pro Pro Val Arg Arg His Arg Asn
                160                 165                 170 ccc aac cgg cct gag tgg aat ggc tat att ccg gga ttc cca att ctc      820
Pro Asn Arg Pro Glu Trp Asn Gly Tyr Ile Pro Gly Phe Pro Ile Leu
            175                 180                 185 atc aac ttt aag gcc acc aag ttc ctg aac tta aat ctc cgc tac tcc      868
Ile Asn Phe Lys Ala Thr Lys Phe Leu Asn Leu Asn Leu Arg Tyr Ser
        190                 195                 200 ttc ctc aag acg gcc tcc ttc ttc gtc cgc ctg ggg ccc atg gca ctg      916
Phe Leu Lys Thr Ala Ser Phe Phe Val Arg Leu Gly Pro Met Ala Leu
    205                 210                 215 gct ttc aaa gtc cgc ggc ctg ttg gac tgc aaa cat tcg tgg aag agg      964
Ala Phe Lys Val Arg Gly Leu Leu Asp Cys Lys His Ser Trp Lys Arg
220                 225                 230                 235 ctg aag gac att agg aaa att ttc cct ggc aag aaa tct gtc gtc tcc     1012
Leu Lys Asp Ile Arg Lys Ile Phe Pro Gly Lys Lys Ser Val Val Ser
                240                 245                 250 gag tac gtg gcc gag cac tgg gca gag gac acc ttc ttt ggg tac cag     1060
Glu Tyr Val Ala Glu His Trp Ala Glu Asp Thr Phe Phe Gly Tyr Gln
            255                 260                 265 tac ctc aac ggc gtc aac ccc ggc ctg atc cgc cgc tgc acg cgg atc     1108
Tyr Leu Asn Gly Val Asn Pro Gly Leu Ile Arg Arg Cys Thr Arg Ile
        270                 275                 280 cca gac aag ttc ccc gtc aca gac gac atg gtg gct ccg ttc ctg ggc     1156
Pro Asp Lys Phe Pro Val Thr Asp Asp Met Val Ala Pro Phe Leu Gly
    285                 290                 295 gag gga acg tgc ttg caa gcg gag ctg gag aag ggg aac att tac ctg     1204
Glu Gly Thr Cys Leu Gln Ala Glu Leu Glu Lys Gly Asn Ile Tyr Leu
300                 305                 310                 315 gcc gac tac cgc atc atg gag ggc atc ccc acc gtg gag ctc agc ggc     1252
Ala Asp Tyr Arg Ile Met Glu Gly Ile Pro Thr Val Glu Leu Ser Gly
                320                 325                 330 cgg aag cag cac cac tgc gcc ccc ctc tgc ctg ctg cac ttt gga ccc     1300
Arg Lys Gln His His Cys Ala Pro Leu Cys Leu Leu His Phe Gly Pro
            335                 340                 345 gag ggc aag atg atg ccc atc gcc atc cag ctc agc cag acc cct ggg     1348
Glu Gly Lys Met Met Pro Ile Ala Ile Gln Leu Ser Gln Thr Pro Gly
        350                 355                 360 cca gat tgc ccc atc ttc ctg ccc agt gat tct gag tgg gac tgg ctg     1396
Pro Asp Cys Pro Ile Phe Leu Pro Ser Asp Ser Glu Trp Asp Trp Leu
    365                 370                 375 cta gcc aag acg tgg gta cgc tat gcg gag ttc tac agc cac gag gcc     1444
Leu Ala Lys Thr Trp Val Arg Tyr Ala Glu Phe Tyr Ser His Glu Ala
380                 385                 390                 395 atc gcc cac ctg ctg gag aca cac ctc att gct gag gcc ttc tgc ctg     1492
Ile Ala His Leu Leu Glu Thr His Leu Ile Ala Glu Ala Phe Cys Leu
                400                 405                 410 gcc ttg ctg agg aac ctg ccc atg tgc cac ccc ctc tac aag ctc ctc     1540
Ala Leu Leu Arg Asn Leu Pro Met Cys His Pro Leu Tyr Lys Leu Leu
            415                 420                 425 atc ccc cat acc cga tac acc gtc cag atc aac agc att ggc cgg gcc     1588
Ile Pro His Thr Arg Tyr Thr Val Gln Ile Asn Ser Ile Gly Arg Ala
```

```
                430                     435                     440
gtt ctc ctc aat gag ggg ggg ctc tct gcc aag ggc atg tcc ctg ggc    1636
Val Leu Leu Asn Glu Gly Gly Leu Ser Ala Lys Gly Met Ser Leu Gly
            445                     450                     455 gtg gaa ggc ttt gct ggg gtg atg gta cgg gct ctg tcg gag ctc acc    1684
Val Glu Gly Phe Ala Gly Val Met Val Arg Ala Leu Ser Glu Leu Thr
460                     465                     470                     475 tat gac agc ctc tac ctc ccc aat gac ttt gtg gag cgt ggg gtc cag    1732
Tyr Asp Ser Leu Tyr Leu Pro Asn Asp Phe Val Glu Arg Gly Val Gln
                480                     485                     490 gac ctg cct gga tat tac tac cgc gat gac agc ttg gcg gtg tgg aat    1780
Asp Leu Pro Gly Tyr Tyr Tyr Arg Asp Asp Ser Leu Ala Val Trp Asn
            495                     500                     505 gca ctg gag aag tat gtg acg gag atc atc acc tat tat tac ccg agt    1828
Ala Leu Glu Lys Tyr Val Thr Glu Ile Ile Thr Tyr Tyr Tyr Pro Ser
        510                     515                     520 gac gca gcc gtg gag ggt gat ccg gaa ttg cag tct tgg gtg cag gaa    1876
Asp Ala Ala Val Glu Gly Asp Pro Glu Leu Gln Ser Trp Val Gln Glu
    525                     530                     535 ata ttt aaa gag tgc ctc ctg ggg cgg gag agc tca ggc ttc cct agg    1924
Ile Phe Lys Glu Cys Leu Leu Gly Arg Glu Ser Ser Gly Phe Pro Arg
540                     545                     550                     555 tgc ttg cga acc gtg cct gag ctg atc cga tat gtc act ata gtc atc    1972
Cys Leu Arg Thr Val Pro Glu Leu Ile Arg Tyr Val Thr Ile Val Ile
                560                     565                     570 tac acc tgc tct gcc aag cac gct gct gtc aac aca ggc cag atg gag    2020
Tyr Thr Cys Ser Ala Lys His Ala Ala Val Asn Thr Gly Gln Met Glu
            575                     580                     585 ttc acc gcc tgg atg ccc aac ttc cca gcg tcc atg cgg aat cca ccg    2068
Phe Thr Ala Trp Met Pro Asn Phe Pro Ala Ser Met Arg Asn Pro Pro
        590                     595                     600 att cag act aag ggg ctg acc act ctg gag acc ttc atg gac acg ttg    2116
Ile Gln Thr Lys Gly Leu Thr Thr Leu Glu Thr Phe Met Asp Thr Leu
    605                     610                     615 ccg gat gtg aag acc acg tgc atc acg ctg ctg gtg ctc tgg acc ctc    2164
Pro Asp Val Lys Thr Thr Cys Ile Thr Leu Leu Val Leu Trp Thr Leu
620                     625                     630                     635 agc cga gag cct gac gac agg cgg ccc ctg gga cac ttc ccg gac att    2212
Ser Arg Glu Pro Asp Asp Arg Arg Pro Leu Gly His Phe Pro Asp Ile
                640                     645                     650 cac ttc gtg gag gag gcc ccg cgg agg agc ata gag gcg ttc cgc cag    2260
His Phe Val Glu Glu Ala Pro Arg Arg Ser Ile Glu Ala Phe Arg Gln
            655                     660                     665 cgc ctg aac cag atc tca cac gac atc cgc cag cgc aac aag tgc ctt    2308
Arg Leu Asn Gln Ile Ser His Asp Ile Arg Gln Arg Asn Lys Cys Leu
        670                     675                     680 ccc atc ccc tac tac tac ctg gac ccg gtg ctg att gag aac agc att    2356
Pro Ile Pro Tyr Tyr Tyr Leu Asp Pro Val Leu Ile Glu Asn Ser Ile
    685                     690                     695 tct att taggagcgcg cttcccgtct ctcctctccc cattctgtgc cctactattt    2412
Ser Ile
700 tcaacaaaac aaaacaaaca agcaaaaaac acaaaaacct cagagaccaa aacacca    2469

<210> SEQ ID NO 2
<211> LENGTH: 701
<212> TYPE: PRT
<213> ORGANISM: Homo sapiens

<400> SEQUENCE: 2
```

```
Met Ala Thr Tyr Lys Val Arg Val Ala Thr Gly Thr Asp Leu Leu Ser
1               5                   10                  15

Gly Thr Arg Asp Ser Ile Ser Leu Thr Ile Val Gly Thr Gln Gly Glu
            20                  25                  30

Ser His Lys Gln Leu Leu Asn His Phe Gly Arg Asp Phe Ala Thr Gly
        35                  40                  45

Ala Val Gly Gln Tyr Thr Val Gln Cys Pro Gln Asp Leu Gly Glu Leu
    50                  55                  60

Ile Ile Ile Arg Leu His Lys Glu Arg Tyr Ala Phe Phe Pro Lys Asp
65                  70                  75                  80

Pro Trp Tyr Cys Asn Tyr Val Gln Ile Cys Ala Pro Asn Gly Arg Ile
                85                  90                  95

Tyr His Phe Pro Ala Tyr Gln Trp Met Asp Gly Tyr Glu Thr Leu Ala
                100                 105                 110

Leu Arg Glu Ala Thr Gly Lys Thr Thr Ala Asp Asp Ser Leu Pro Val
        115                 120                 125

Leu Leu Glu His Arg Lys Glu Ile Arg Ala Lys Gln Asp Phe Tyr
        130                 135                 140

His Trp Arg Val Phe Leu Pro Gly Leu Pro Ser Tyr Val His Ile Pro
145                 150                 155                 160

Ser Tyr Arg Pro Pro Val Arg Arg His Arg Asn Pro Asn Arg Pro Glu
                165                 170                 175

Trp Asn Gly Tyr Ile Pro Gly Phe Pro Ile Leu Ile Asn Phe Lys Ala
                180                 185                 190

Thr Lys Phe Leu Asn Leu Asn Leu Arg Tyr Ser Phe Leu Lys Thr Ala
                195                 200                 205

Ser Phe Phe Val Arg Leu Gly Pro Met Ala Leu Ala Phe Lys Val Arg
        210                 215                 220

Gly Leu Leu Asp Cys Lys His Ser Trp Lys Arg Leu Lys Asp Ile Arg
225                 230                 235                 240

Lys Ile Phe Pro Gly Lys Lys Ser Val Val Ser Glu Tyr Val Ala Glu
                245                 250                 255

His Trp Ala Glu Asp Thr Phe Phe Gly Tyr Gln Tyr Leu Asn Gly Val
                260                 265                 270

Asn Pro Gly Leu Ile Arg Arg Cys Thr Arg Ile Pro Asp Lys Phe Pro
        275                 280                 285

Val Thr Asp Asp Met Val Ala Pro Phe Leu Gly Glu Gly Thr Cys Leu
        290                 295                 300

Gln Ala Glu Leu Glu Lys Gly Asn Ile Tyr Leu Ala Asp Tyr Arg Ile
305                 310                 315                 320

Met Glu Gly Ile Pro Thr Val Glu Leu Ser Gly Arg Lys Gln His His
                325                 330                 335

Cys Ala Pro Leu Cys Leu Leu His Phe Gly Pro Glu Gly Lys Met Met
                340                 345                 350

Pro Ile Ala Ile Gln Leu Ser Gln Thr Pro Gly Pro Asp Cys Pro Ile
                355                 360                 365

Phe Leu Pro Ser Asp Ser Glu Trp Asp Trp Leu Leu Ala Lys Thr Trp
        370                 375                 380

Val Arg Tyr Ala Glu Phe Tyr Ser His Glu Ala Ile Ala His Leu Leu
385                 390                 395                 400

Glu Thr His Leu Ile Ala Glu Ala Phe Cys Leu Ala Leu Leu Arg Asn
                405                 410                 415
```

-continued

```
Leu Pro Met Cys His Pro Leu Tyr Lys Leu Leu Ile Pro His Thr Arg
            420                 425                 430

Tyr Thr Val Gln Ile Asn Ser Ile Gly Arg Ala Val Leu Leu Asn Glu
        435                 440                 445

Gly Gly Leu Ser Ala Lys Gly Met Ser Leu Gly Val Glu Gly Phe Ala
    450                 455                 460

Gly Val Met Val Arg Ala Leu Ser Glu Leu Thr Tyr Asp Ser Leu Tyr
465                 470                 475                 480

Leu Pro Asn Asp Phe Val Glu Arg Gly Val Gln Asp Leu Pro Gly Tyr
                485                 490                 495

Tyr Tyr Arg Asp Asp Ser Leu Ala Val Trp Asn Ala Leu Glu Lys Tyr
            500                 505                 510

Val Thr Glu Ile Ile Thr Tyr Tyr Pro Ser Asp Ala Ala Val Glu
        515                 520                 525

Gly Asp Pro Glu Leu Gln Ser Trp Val Gln Glu Ile Phe Lys Glu Cys
    530                 535                 540

Leu Leu Gly Arg Glu Ser Ser Gly Phe Pro Arg Cys Leu Arg Thr Val
545                 550                 555                 560

Pro Glu Leu Ile Arg Tyr Val Thr Ile Val Ile Tyr Thr Cys Ser Ala
                565                 570                 575

Lys His Ala Ala Val Asn Thr Gly Gln Met Glu Phe Thr Ala Trp Met
            580                 585                 590

Pro Asn Phe Pro Ala Ser Met Arg Asn Pro Pro Ile Gln Thr Lys Gly
        595                 600                 605

Leu Thr Thr Leu Glu Thr Phe Met Asp Thr Leu Pro Asp Val Lys Thr
    610                 615                 620

Thr Cys Ile Thr Leu Leu Val Leu Trp Thr Leu Ser Arg Glu Pro Asp
625                 630                 635                 640

Asp Arg Arg Pro Leu Gly His Phe Pro Asp Ile His Phe Val Glu Glu
                645                 650                 655

Ala Pro Arg Arg Ser Ile Glu Ala Phe Arg Gln Arg Leu Asn Gln Ile
            660                 665                 670

Ser His Asp Ile Arg Gln Arg Asn Lys Cys Leu Pro Ile Pro Tyr Tyr
        675                 680                 685

Tyr Leu Asp Pro Val Leu Ile Glu Asn Ser Ile Ser Ile
    690                 695                 700

<210> SEQ ID NO 3
<211> LENGTH: 28
<212> TYPE: DNA
<213> ORGANISM: Homo sapiens

<400> SEQUENCE: 3
caacttccca gcgtccatgc gtaatcca                                         28

<210> SEQ ID NO 4
<211> LENGTH: 30
<212> TYPE: DNA
<213> ORGANISM: Homo sapiens

<400> SEQUENCE: 4
tggtgttttg gtctctgagg tttttgtgtt                                       30

<210> SEQ ID NO 5
<211> LENGTH: 30
<212> TYPE: DNA
<213> ORGANISM: Homo sapiens
```

```
<400> SEQUENCE: 5
tggtgttttg gtctctgagg tttttgtgtt                                    30

<210> SEQ ID NO 6
<211> LENGTH: 29
<212> TYPE: DNA
<213> ORGANISM: Homo sapiens

<400> SEQUENCE: 6
tttttgcttg tttgttttgt tttgttgaa                                     29

<210> SEQ ID NO 7
<211> LENGTH: 23
<212> TYPE: DNA
<213> ORGANISM: Homo sapiens

<400> SEQUENCE: 7
ttgggccttc gtgtggccct cca                                           23

<210> SEQ ID NO 8
<211> LENGTH: 24
<212> TYPE: DNA
<213> ORGANISM: Homo sapiens

<400> SEQUENCE: 8
agcgcgctcc taaatagaaa tgct                                          24

<210> SEQ ID NO 9
<211> LENGTH: 20
<212> TYPE: DNA
<213> ORGANISM: Homo sapiens

<400> SEQUENCE: 9
tgcctgctgc actttggacc                                               20

<210> SEQ ID NO 10
<211> LENGTH: 22
<212> TYPE: DNA
<213> ORGANISM: Homo sapiens

<400> SEQUENCE: 10
tggtcttcac atccggcaac gt                                            22

<210> SEQ ID NO 11
<211> LENGTH: 28
<212> TYPE: DNA
<213> ORGANISM: Homo sapiens

<400> SEQUENCE: 11
caacttccca gcgtccatgc gtaatcca                                      28

<210> SEQ ID NO 12
<211> LENGTH: 30
<212> TYPE: DNA
<213> ORGANISM: Homo sapiens

<400> SEQUENCE: 12
tggtgttttg gtctctgagg tttttgtgtt                                    30
```